US009733206B2

(12) United States Patent
Miller et al.

(10) Patent No.: US 9,733,206 B2
(45) Date of Patent: Aug. 15, 2017

(54) SOIL CHEMISTRY SENSOR

(71) Applicant: PLANT BIOSCIENCE LIMITED, Norfolk (GB)

(72) Inventors: Tony Miller, Norwich (GB); Pierre-Henri Le Besnerais, Norwich (GB); Hugo Malaurie, Norwich (GB)

(73) Assignee: Plant Bioscience Limited, Norwich (GB)

( * ) Notice: Subject to any disclaimer, the term of this patent is extended or adjusted under 35 U.S.C. 154(b) by 124 days.

(21) Appl. No.: 14/652,515

(22) PCT Filed: Dec. 20, 2013

(86) PCT No.: PCT/GB2013/053377
§ 371 (c)(1),
(2) Date: Jun. 16, 2015

(87) PCT Pub. No.: WO2014/096844
PCT Pub. Date: Jun. 26, 2014

(65) Prior Publication Data
US 2015/0323491 A1  Nov. 12, 2015

(30) Foreign Application Priority Data

Dec. 21, 2012  (GB) .................................. 1223167.6

(51) Int. Cl.
*G01N 27/403* (2006.01)
*G01N 33/24* (2006.01)

(52) U.S. Cl.
CPC ......... *G01N 27/4035* (2013.01); *G01N 33/24* (2013.01)

(58) Field of Classification Search
CPC ........................... G01N 27/4035; G01N 33/24
See application file for complete search history.

(56) References Cited

U.S. PATENT DOCUMENTS 4,565,666 A * 1/1986 Cahalan ............. G01N 27/4035
204/414
4,834,101 A   5/1989 Collison et al.
(Continued)

FOREIGN PATENT DOCUMENTS

GB       1593270       7/1981
WO   2009157755 A2   12/2009

OTHER PUBLICATIONS

International Preliminary Report on Patentability for corresponding PCT/GB2013/053377 dated Jun. 23, 2013; Completed by Athina Nickitas-Etienne.

(Continued)

*Primary Examiner* — Arun S Phasge
(74) *Attorney, Agent, or Firm* — Tarolli, Sundheim, Covell & Tummino LLP

(57) ABSTRACT

We describe a soil chemistry sensor for in-situ soil chemistry sensing, the sensor comprising a probe incorporating a first, ion-selective electrode and a second, reference electrode, wherein said ion-selective electrode comprises a first-electrode housing defining a first lumen having an ion-selective plug towards a distal end, said first-electrode including a first conductor in a first electrolyte, wherein said reference electrode comprises a second electrode housing defining a second lumen having a porous reference electrode plug towards a distal end, said second electrode including a second conductor in a second electrolyte, wherein said ion-selective plug and said porous reference electrode plug are within 10 mm of one another, and wherein said porous reference electrode plug and said ion-selective plug each comprise a polymer.

20 Claims, 22 Drawing Sheets

(56) References Cited

U.S. PATENT DOCUMENTS

| | | | |
|---|---|---|---|
| 5,677,031 | A | 10/1997 | Allan et al. |
| 5,830,338 | A | 11/1998 | Seto et al. |
| 5,985,117 | A | 11/1999 | Bachas et al. |
| 6,398,931 | B1 | 6/2002 | Burchette et al. |
| 2006/0249386 | A1 | 11/2006 | Bower et al. |
| 2009/0166520 | A1 | 7/2009 | Tuli et al. |
| 2011/0048971 | A1 | 3/2011 | Bower et al. |

OTHER PUBLICATIONS

Ito et al., "Development of a Nitrate Ion-Selective Electrode Based on an Urushi Matrix Membrane and its Application to the Direct Measurement of Nitrate-Nitrogen in Upland Soils", Talanta, 43, 1996, pp. 1869-1881.
International Search Report and Written Opinion for PCT/GB2013/053377, mailed May 6, 2014, pp. 1-16.
Examination Report under Section 18(3) for GB1223167.6, mailed Feb. 9, 2015, pp. 1-3.
Search Report under Section 17(5) for GB1223167.6, mailed Aug. 15, 2013, pp. 1-4.
Examination Report under Section 18(3) for GB1223167.6, mailed Apr. 24, 2015, pp. 1-3.
Fontananova, Enrica, et al. "Effect of additives in the casting solution on the formation of PVDF membranes." Desalination 192.1-3 (2006): 190-197.

\* cited by examiner

SOIL CHEMISTRY SENSOR

RELATED APPLICATIONS

The present invention is a U.S. National Stage under 35 USC 371 patent application, claiming priority to Serial No. PCT/GB2013/053377, filed on 20 Dec. 2013; which claims priority from GB 1223167.6, filed 21 Dec. 2012, the entirety of both of which are incorporated herein by reference.

FIELD OF THE INVENTION

This invention relates to soil chemistry sensors, in particular for sensing nitrate levels, and to the fabrication and use of such sensors.

BACKGROUND TO THE INVENTION

Inorganic fertilisers, in particular nitrogen-based fertilisers, have revolutionised agriculture. However effective management of the amount of fertiliser used on land is important for many reasons including economic efficiency and environmental management—excess nitrogen run off from agriculture can enter drinking water causing significant human health concerns, and can also damage fresh water and marine eco-systems. Various techniques are known for monitoring the nitrate level in soil. Typically a soil core is taken, the nitrogen is extracted, and this is then used to predict the amount of nitrogen available to the roots of plants in the soil. However this is a time consuming process typically involving taking a number of soil cores and waiting on average two weeks for the results to come back from the laboratory. Based on the results a farmer will decide, for example, how much nitrate-based fertiliser to use in a spring and/or autumn application.

This procedure is cumbersome, slow and expensive and there is a need for improved techniques, and in particular effective but relatively inexpensive techniques. Such techniques would also be of use in the developing world.

Adamchuk et al (Adamchuk, V., Lund, E., Sethuramasamyraja, B., Morgan, M., Dobermann, A. and Marx, D., 2005. Direct Measurement of Soil Chemical Properties on-the-Go using Ion-Selective Electrodes. *Computers and Electronics in Agriculture*, vol. 48, no. 3, pp. 272-294) provides a relatively recent review of soil sensing techniques, but all the techniques described there involve extracting a soil sample and analysing it afterwards in an aqueous solution. Ito et al (Ito, S., Baba, K., Asano, Y., Takesako, H., 1996. Development of a Nitrate Ion-Selective Electrode Based on an Urushi Matrix Membrane and its Application to the Direct Measurement of Nitrate Nitrogen in Upland Soils. *Talanta*, vol. 43, no. 11, pp. 1869-1881) describes a nitrate ion-selective electrode based on Urushi, a natural oriental lacquer. Earlier work by one of the inventors (Miller, A. J. and Zhen R-G., *Measurement of intracellular nitrate concentrations in Chara using nitrate-selective microelectrodes*, Planta 1991 184:47-52) describes the fabrication of nitrate-selective microelectrodes for measuring nitrate concentrations in plant cells.

There is a need for improvements in measuring/monitoring the levels of nitrate (and other plant nutrients).

SUMMARY OF THE INVENTION

According to the present invention there is therefore provided [as claim 1].

The inventors have established that for in-situ sensing of soil chemistry, that is sensing by inserting the probe directly into the soil, one key difficulty in practice is ensuring effective operation of the reference electrode. In embodiments this is addressed by fabricating the reference electrode plug or membrane in a similar manner to that used for the ion-selective electrode plug/membrane, in particular by solvent-casting a polymer material into the end of the lumen, for example high molecular weight PVC (polyvinyl chloride). In some preferred embodiments this material includes one or more additives to lower its electrical resistance.

It has also been found to be important to keep the ion-selective and reference electrodes, more particularly their porous plugs, adjacent to one another, for example separated by less than 20, 15, 10, 5, 3, or most preferably 2 millimeters. This is because soil moisture content can vary and with wider spacings the results can be unreliable, becoming overly-dependent on soil moisture level. In preferred embodiments a fastening means is provided around the distal ends of the electrodes to inhibit these from moving apart during insertion into the soil.

For related reasons it has also been found to be important to make the sensor waterproof (except for the porous plugs). Thus preferably the ion-sensing and reference electrodes are sealed within a waterproof enclosure, in embodiments fabricated from cold-shrink tubing: such material is able to achieve a tight seal without the application of heat, which is important for practical fabrication of the probe.

In some preferred embodiments the second, reference electrode is a double junction electrode, in particular including a second electrode chamber connecting with the first via a second porous plug, preferably also fabricated from a polymer material, in a similar manner to the outer porous reference electrode plug. In practical trials the use of a double junction has been found to provide more stable results (sensing signals) and improved probe lifetime, as well as better protection for the probe overall when used in soil.

In embodiments the soil chemistry sensor, more particularly the probe, incorporates soil moisture sensing means such as a pair of exposed electrical conductors. This allows the soil moisture content to be sensed so that, optionally, the signal from the ion-selective electrode may be compensated for the amount of soil moisture present. In principle, however, such soil moisture compensation may be performed using a separate sensor.

In some preferred implementations the soil chemistry sensor is provided in combination with a high input impedance voltage sensor to sense the voltage from the probe. Advantageously a probe may be provided with a wireless data transmitter, for example a Wi-Fi and/or mobile phone network transmitter to communicate sensor data from the probe. Where a wired connection to the probe is employed this can tend to guide rainwater (along the outside of the wire) affecting the local nitrate levels.

In one preferred implementation a plurality of probes is connected to a shared data logger, which may have a (shared) wireless network connection for exporting captured data, via one or more voltage sensors (one sensor may be multiplexed across a plurality of probes). This facilitates, for example, the soil chemistry to be measured at multiple different depths within the soil, say 30 cm, 60 cm and 90 cm, and/or at multiple different locations within a field. This can provide improved data for more efficient applications of fertiliser by varying the application of fertiliser with location within a field and/or dependent on a measured profile of soil chemistry according to depth. In embodiments a probe or set of probes may include a temperature sensor for adjusting or compensating measurement signals for temperature for improved accuracy.

The invention also provides a method of collecting soil chemistry data directly from soil, in particular by inserting a probe as described above into the soil.

The use of a probe, or multiple probes, as described above facilitates measuring/monitoring the actual levels of a plant nutrient in the soil, which can change quite dynamically over time and/or other conditions such as moisture level and the like.

A low-cost sensor is desirable, for example for developing world applications, and also when wishing to deploy multiple sensors over an area of agricultural land. It has been found that effective electrodes can be fabricated from a disposable plastic pipette tip (for example of, PVC or polypropylene). Preferably the plugs are then formed by solvent-casting a polymer again, for example PVC, as previously described. In such a case it has been found that increased reliability can be obtained by treating the lumen of an electrode in which the plug is being formed so as to increase its internal hydrophobicity. This may be achieved in various ways including, for example, by plasma treatment but in one straightforward approach an emulsion of polydimethylsiloxane, silica filler and non-ionic emulsifier (Dow Corning® Repelcote) is employed.

Some preferred embodiments of the above described soil chemistry sensor are used for in-situ soil nitrate level sensing, but depending upon the ion-selective material employed in the first electrode plug other chemicals relevant to environmental monitoring and/or plant nutrition may also be sensed including, but not limited to: ammonium, potassium and phosphorous; variants of the sensor may also be employed for sensing soil pH.

In embodiments, the above-described soil chemistry sensor is used for identifying a soil chemistry depletion zone around a plant root. A nutrient depletion zone develops around a root when nutrients are removed from the soil solution faster than they can be replaced by the movement of nutrients through the solution. For example, ions which have low mobility in the solution may produce a sharp/narrow depletion zone close to the root.

In embodiments, a plurality of soil chemistry sensors are used for determining soil chemistry data at a plurality of depths in a soil sample. This may enable determination of how chemicals move through soil (without any plants), and/or how chemicals are absorbed by plant root systems. For example, roots close to the surface of soil may absorb chemicals in the soil at a different rate to those deeper in the soil.

The soil chemistry sensors described thus far are capable of measuring the soil chemistry in situ at a certain distance below the surface of the soil, where the distance itself (i.e. depth) is limited by the length of sensor/sensor electrodes. It may be desirable to measure the soil chemistry deeper in a soil structure in a field, and/or to measure the soil chemistry at multiple different depths in a soil structure simultaneously, and/or to obtain real-time soil chemistry data in situ. If real-time measurements indicate that fertilizer needs to be added to the top of the soil, but that the soil is prone to leaching, then a farmer may use the information to decide when to irrigate after applying fertilizer to his crops to minimise the effect of the water washing away the nitrates from near the top of the soil surface.

Thus, an aspect of the present invention provides a probe for in situ soil chemistry sensing, the probe comprising: a longitudinally extending housing with a tip for penetrating soil, said housing having at least one sensing region, wherein said sensing region comprises at least one sensing membrane to permit ions from said soil to enter said probe, and wherein said sensing region is on a lateral wall of said housing displaced away from (i.e. near but not on) said tip of said probe.

In embodiments, the sensing region comprises a pair of said membranes, an ion-selective membrane and a reference membrane, for respective ion-selective and reference electrodes of a sensor within said probe.

In embodiments, the sensor comprises conductive electrolyte or gel between each respective membrane and a respective electrode connection.

A further related aspect of the invention provides a sensor for in situ soil chemistry sensing comprising a pair of membranes in a common surface, an ion-selective membrane and a reference membrane for respective ion-selective and reference electrodes of the sensor and conductive electrolyte or gel between each respective membrane and a respective electrode connection.

An aspect of the invention provides a probe for in-situ soil chemistry sensing, said probe comprising: one or more soil chemistry sensors, wherein each of said one or more soil chemistry sensors comprises: a first reference membrane and a second ion-selective membrane, a first electrical connection coupled to said first reference membrane; and a second electrical connection coupled to said second ion-selective membrane; wherein said first and said second electrical connections provide a soil chemistry sensing signal; and a tube comprising one or more sensing apertures along a length of said tube, wherein one of said one or more sensors is provided in one of said one or more apertures, and wherein said probe is capable of said soil chemistry sensing at one or more depths below a soil surface.

In embodiments, each of the soil chemistry sensors is detachably attached to said tube in said apertures.

In preferred embodiments, the first reference membrane and the second ion-selective membrane are close together, preferably within 2 mm of one another.

In a related aspect of the invention, there is provided a method of providing nutrients to a plant, said method comprising: inserting a probe, in particular as described above, vertically into soil around said plant; sensing soil chemistry at one or more depths below a surface of said soil; identifying depletion of said nutrients at said one or more depths below said surface of said soil; applying nutrients to said soil in response to said depletion.

In embodiments, the sensing occurs at a first depth close to said surface of said soil and a second depth further away from said surface of said soil, and further wherein said nutrients are depleted if said nutrient concentration at said first depth is relatively less than said nutrient concentration at said second depth, preferably 10-fold less.

A further aspect of the invention provides use of a soil chemistry sensor/probe, for determining when to apply fertilizer to a plant, the method comprising: sensing a level of nutrient at a plurality of different depths in the vicinity of said plant, using the sensor/probe, wherein said depths identify a nutrient depletion zone, said nutrient depletion zone comprising a region, defined by depth, where uptake of said nutrient by said plant is relatively greater; determining a ratio of sensed nutrient levels between at least two of said different depths to determine an uptake of said nutrient by said plant from a relative depletion of said nutrient at one of said depths with respect to another; and determining when to apply said fertilizer based on said determined ratio.

BRIEF DESCRIPTION OF THE DRAWINGS

These and other aspects of the invention will now be further described, by way of example only, with reference to the accompanying figures in which:

FIGS. 10b and 10c illustrate construction of the probe of FIG. 10a;

FIGS. 11b and 11c depict two different arrangements for the horizontal soil chemistry sensors of FIG. 11a;

FIG. 12b shows a zoomed-in view of the 'button-style' soil chemistry sensor of FIG. 12a;

DETAILED DESCRIPTION OF PREFERRED EMBODIMENTS

Figure 1:
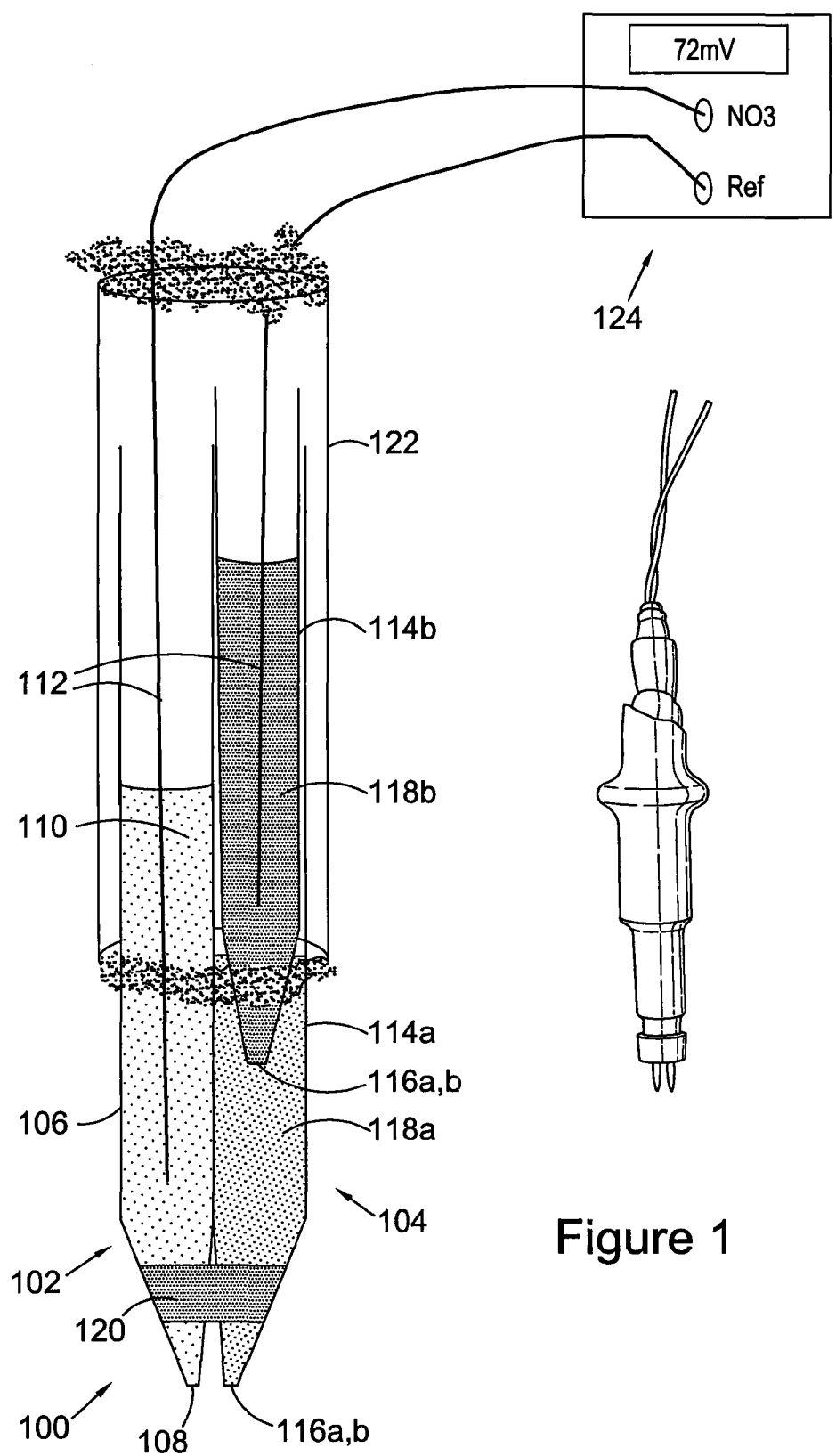
FIG. 1 shows a soil chemistry sensor according to an embodiment of the invention (the inset shows an actually-constructed embodiment)

FIG. 1 shows a nitrate ($NO_3$)-selective soil chemistry sensor 100 according to an embodiment of the invention. The sensor comprises a nitrate-selective electrode 102 and a double junction reference electrode 104. The ion-selective electrode comprises a plastic lumen at 106, in embodiments fabricated from a disposable pipette tip or plastic syringe such as a polypropylene Distritip® syringe, for low cost. An ion-selective membrane 108 is fabricated at the end of the electrode by solvent-casting a polymer such as high molecular weight PVC in combination with an ion carrier. For example for nitrate sensing a suitable ion carrier is tridodecylmethylammonium (TDDMA) nitrate, although additionally or alternatively other ion-selective components may be employed to additionally or alternatively sense other plant nutrients. The membrane composition may be dissolved, for example, in tetrahydrofuran (THF).

An example ion-selective composition for fabricating a nitrate-selective membrane is as follows:
1.50 wt % Tridodecylmethylammonium nitrate
16.25 wt % 2-Nitrophenyl octyl ether
1.93 wt % Nitrocellulose, 35% in isopropanol
0.25 wt % Methyltriphenylphosphonium bromide
5.75 wt % Poly(vinyl chloride) high molecular weight
74.32 wt % Tetrahydrofuran Preferably the plastic interior of the lumen is treated with a silanizing solution such as Dow Corning® repelcote to improve the hydrophobicity of the surface of the plastic, to improve the sealing between the solvent-cast membrane and lumen. After this has thoroughly dried, the end portion of the lumen is filled with the dissolved ion-selective composition and the THF allowed to evaporate gradually over a number of hours at room temperature. The electrode is then filled with an electrolyte 110 comprising, for example, 100 mM $KCl+100$ mM $KNO_3$, in which is located an Ag/AgCl (chlorided silver) electrode wire 112.

Preferably the reference electrode 104 is a double junction reference electrode comprising a pair of plastic lumen 114a,b, each with a solvent-cast reference membrane 116a,b fabricated as previously described except that the TDDMA nitrate ion carrier is omitted. The reference membrane composition may also include one or more additives to improve the electrical conductivity of this membrane.

In the double junction reference electrode different outer 118a and inner 118b filling solutions are employed. The inner filling solution may be 100 mM KCl; the outer filling solution may comprise, for example, 100 mM ammonium sulphate (for nitrate sensing) or 100 mM magnesium sulphate (for $NH_4$ sensing) or 100 mM sodium chloride (for potassium sensing). Further examples of solution compositions, for sensing different ions, and pH, are given later.

In some preferred embodiments the tips of the ion-selective and reference electrodes are fastened at 120 together by tape and/or rubber sleeves; preferably the membrane tips are only 1-2 mm apart. It is also important for the probe to be waterproof, and this was achieved by sealing the probe with cold-shrink tubing 122 (a pre-stretched elastomer which shrinks upon removal of the supporting core during application), in combination with silicone sealant. This provided an effective seal without the need for heating, which can damage the electrodes.

As schematically illustrated in FIG. 1 the silver/silver chloride electrode wires 112 are coupled to a high import impedance volt meter, for example a differential electrometer. The potential across the wires 112 is a function of the selected, for example nitrate ion concentration. The closer to 100 mM nitrate (the level of nitrate ions in the solution in the ion-selective electrode) the closer the potential is to 0V. When the nitrate (or other ion) concentration in the external environment decreases, the voltage increases, according to a variation of the Nernst equation, the Nickolsky-Eisenman equation (which takes into account interference from ions other than the target ion):

$$E = K + (2.303RT/z_iF)\log(a_i + k_{ij}a_j^{Z_i/Z_j})$$

where E is the potential, $z_i$ and $a_i$ are the charge and activity of the ion of interest, K is a constant dependent on the probe design, R is the gas constant, T is temperature in Kelvin, F is the Faraday constant, j labels the interfering ions and $k_{ij}$ is the selectivity coefficient—a quantitative measurement of the ability of the electrode to discriminate against interfering ion j.

Figure 2:
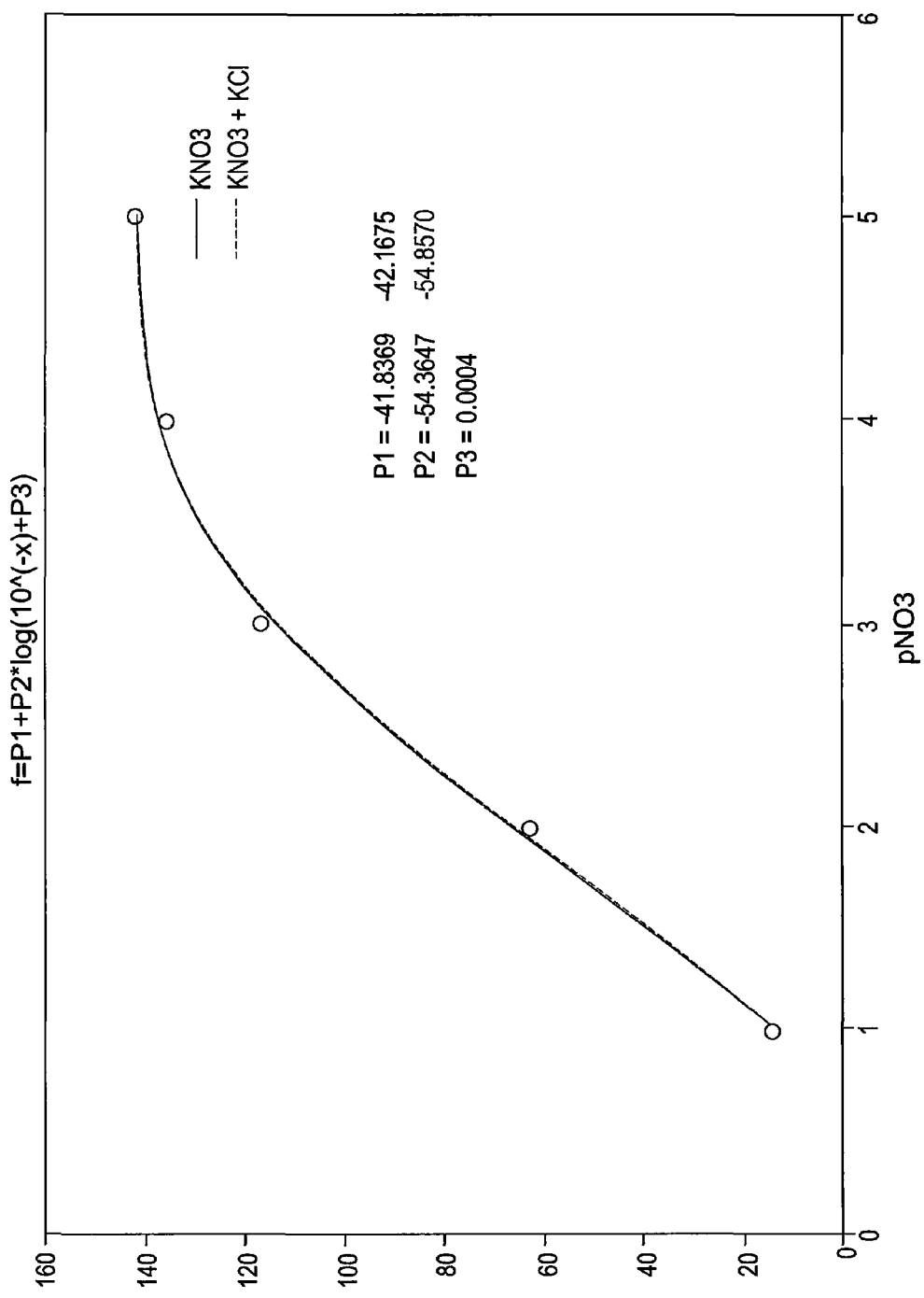
FIG. 2 shows a calibration curve for the sensor of FIG. 1.

Prior to use the probe is calibrated using a set of nitrate solutions which have a constant background ionic strength, for example with nitrate activity of 100 mM ($pNO_3$), 10 mM, 1 mM, 0.1 mM and 0.01 mM. FIG. 2 shows an example calibration curve in which the points are the measured voltages at the different nitrate concentrations and the line is a Nickolsky-Eisenman curve fitted to the equation below:

$$f = P1 + P2*\log(10^{\wedge}(-x) + P3)$$

In this equation the slope, P2 is approximately 58 mV and the value of P3 defines the limited detection of the probe (in M). FIG. 2 shows two curves, a second curve with 10 mM of KCl added to each nitrate solution. Chloride ions can interfere with nitrate-selective membranes but the two curves in FIG. 2 are substantially coincident, showing that the presence of chloride ions has almost no effect on measurements from embodiments of the probe.

The table below shows one example of a set of soil chemistry measurements made using an embodiment of the probe—stable, consistent readings were obtained.

| Parameters | EMF = P1 + P2 · log(a + P3) | NO3 Measures |
|---|---|---|
| P1 | −26.2614 | |
| P2 | −54.1356 | |
| P3 | 3.89E−06 | |

Time series measurements could establish the effectiveness of uptake of nitrate by plants in the soil under test. Calibrations before and after time series measurements indicated little or no drift in the probe data.

Monitoring the actual levels of nitrate in soil shows that these vary quite substantially with time and a location, even within a single field. It is desirable to be able to track these variations and/or to monitor nitrate (or other plant nutrient) levels at different depths within the soil, for example 30 cm, 60 cm and 90 cm deep.

Figure 3:
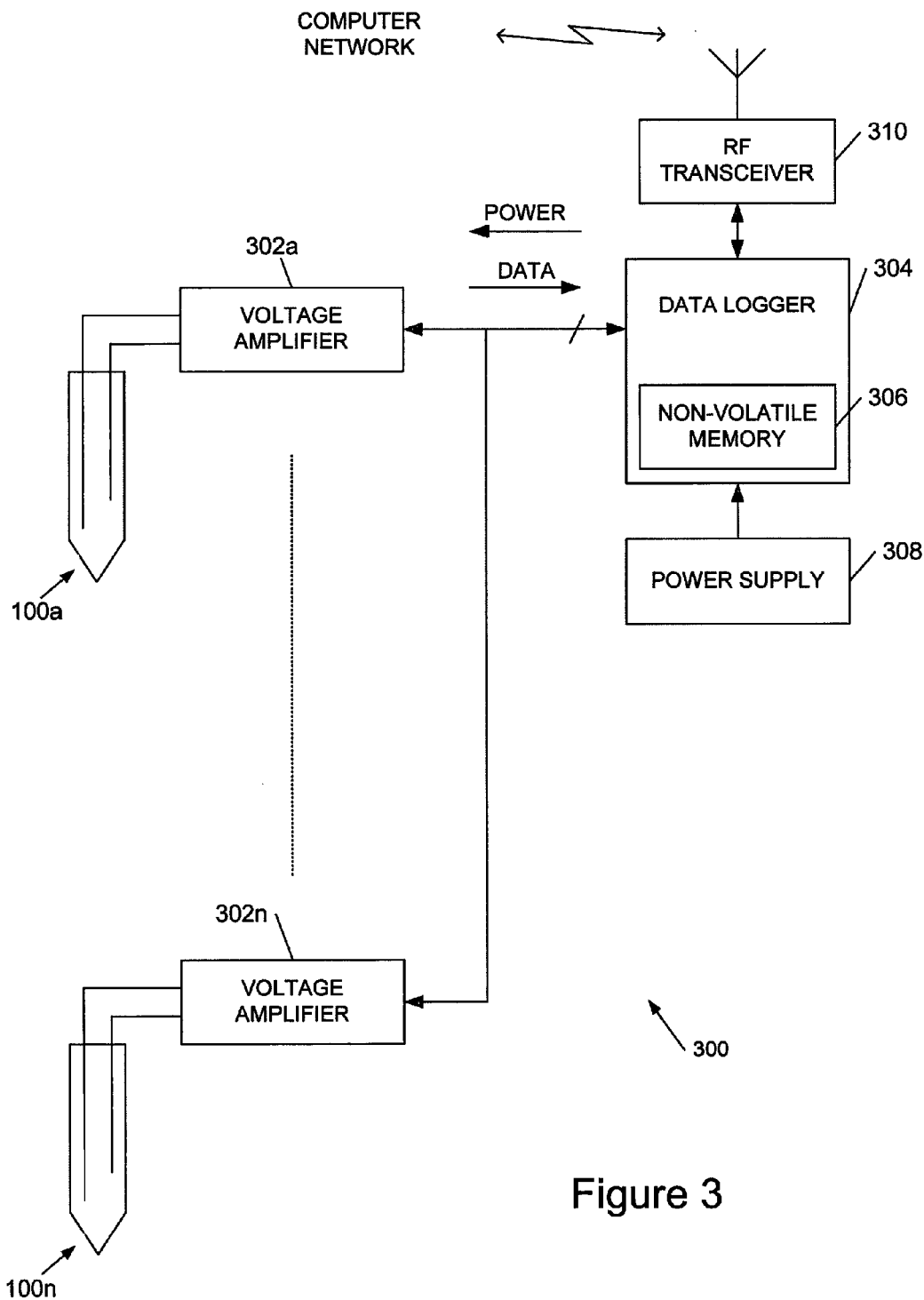
FIG. 3 shows a sensor system incorporating multiple soil chemistry sensors of the type shown in FIG. 1.

FIG. 3 shows an embodiment of a system 300 including a plurality of probes 100a-n each as previously described, each coupled to a respective voltage amplifier 302a-n which provides voltage data to a data logger 304. In this example the probes are coupled to the data logger via a wired connection which is used to power the probes/amplifiers, but in other embodiments a wireless connection may be employed. The data logger 304 preferably incorporates non-volatile memory 306 to store the collected data and an RF transceiver 310, for example, to communicate with a computer or mobile phone network, to provide a link to a remote data collection/analysis computer/network. A power supply 308 for the system may comprise, for example, a rechargeable battery, optionally powered from a renewable energy source such as wind or solar power.

| Date Place | Time | Electrode 1 | Electrode 2 | Electrode 3 | Average (mV) | Nitrate activity (mM) | Temp given | Temperature celcius |
|---|---|---|---|---|---|---|---|---|
| Water | | 270 | 270 | 270 | 270 | −0.000523128 | | |
| Silver sand washed + water | | 205 | 205 | 205 | 205 | 0.049578314 | | |
| Silver sand washed + 0.1 mM NO3 | | 201 | 201 | 201 | 201 | 0.059495063 | | |
| Linosa (3 pt) + water | | 199 | 199 | 199 | 199 | 0.065123179 | | |
| Linosa (3 pt) + 0.1 mM NO3 | | 180 | 180 | 180 | 180 | 0.150958781 | | |
| Linosa (3 pt) + water | | 196 | 196 | 196 | 196 | 0.074516048 | | |
| Linosa (3 pt) + 0.1 mM NO3 | | 196 | 196 | 196 | 196 | 0.074516048 | | |
| Piriddu (3 pt) + water | | 173 | 173 | 173 | 173 | 0.204661734 | | |
| Piriddu (3 pt) + 0.1 mM NO3 | | 187 | 187 | 187 | 187 | 0.111084466 | | |
| Linosa (1 pt) + water | | 171 | 171 | 171 | 171 | 0.22317925 | | |
| Linosa (1 pt) + 0.1 mM NO3 | | 178 | 178 | 178 | 178 | 0.164707993 | | |
| UC82 (1 pt) + water | | 141 | 141 | 141 | 141 | 0.809547861 | | |
| UC82 (1 pt) + 0.1 mM NO3 | | 156 | 156 | 156 | 156 | 0.425885519 | | |

Further Example Compositions

Further example ion-selective compositions for fabricating other ion-selective membranes are given below. Preferably High molecular weight poly(vinyl chloride) (PVC) is used in all the membranes.

Ammonium

An example ammonium sensor component is nonactin, sold by Sigma-Aldrich (Ammonium ionophore I). The electrode detection limit 11 μM ammonium, but high $K^+$ can interfere with the response.

| Component (wt %) | % |
| --- | --- |
| Sensor—nonactin | 5% |
| 2-nitrophenyl octyl ether (plasticiser) | 64% |
| Potassium tetrakis (4-Chlorophenyl) borate (additive) | 1% |
| PVC matrix | 30% |

Calcium

An example calcium sensor component is again sold by Sigma-Aldrich as calcium ionophore II (product number 21193).

| Component (wt %) | % |
| --- | --- |
| Sensor—ETH129 | 1% |
| 2-nitrophenyl octyl ether (plasticiser) | 65.6% |
| Potassium tetrakis (4-Chlorophenyl) borate (additive) | 0.6% |
| PVC matrix | 32.8% |

Potassium

An example ammonium sensor is 90% (w/w) potassium ionophore cocktail and 10% (w/w) PVC polymer. The potassium ionophore cocktail contains:
5 wt % potassium ionophore (Sigma product number 60403) valinomycin.
93 wt % 1,2 dimethyl-3-notrobenzene (Sigma product number 40870).
2 wt % potassium tetrakis(4-chlorophenyl) borate (Sigma product number 60591).

| Component (wt %) | % |
| --- | --- |
| Sensor—valinomycin | 5% |
| 1,2 dimethyl-3-nitrobenzene (plasticiser) | 93% |
| Potassium tetrakis (4-Chlorophenyl) borate (additive) | 2% |

Phosphate

An example phosphate sensor component may be based on the phosphate sensor of Carey C M & Riggan W B Anal Chem. 1994 Nov. 1; 66(21):3587-91, a cyclic polyamine ionophore for use in a dibasic phosphate-selective electrode. Further details can be found in EP2376442A, to which reference may be made. The composition is similar to that used for nitrate.

| Component (wt %) | % |
| --- | --- |
| Sensor—Carey & Riggan 1994 | 6% |
| 2-nitrophenyl octyl ether (plasticiser) | 65% |
| Methyltriphenylphosphonium (additive) | 1% |
| PVC matrix | 23% |
| nitrocellulose | 5% |

In addition reference may be made to Kim et al. 2007 Transactions of ASABE 50(2):415-425 which shows that similar cobalt sensors may be fabricated.

pH (Protons)

One example pH sensor molecule is ETH1907 (Hydrogen ionophore II), sold commercially by Sigma-Aldrich. Like the nitrate sensor mix, this pH cocktail is made with a PVC and nitrocellulose solid matrix, 62% pH cocktail, 28% PVC and 10% blotting nitrocellulose (Sigma-Aldrich product code N8267 Sigma).

A suitable cocktail mix (as tabulated below) is sold by Sigma-Aldrich (product code 95297).

| Component (wt %) | % |
| --- | --- |
| Sensor—ETH1907 | 6% |
| 2-nitrophenyl octyl ether (plasticiser) | 93% |
| Potassium tetrakis (4-Chlorophenyl) borate (additive) | 1% |

Sodium

For sodium reference may be made to Carden et al. 2001 (J. Exp. Bot. 52: 1353) which describes an improved sodium sensor (improved $Na^+$ to $K^+$ selectivity).

| Component (wt %) | % |
| --- | --- |
| Sensor—sodium ionophore* | 1% |
| Bis (1-butylpentyl) adipate (plasticiser)—(Sigma product Number 02150) | 65.9% |
| Potassium tetrakis (4-Chlorophenyl) borate (additive) | 0.6% |
| PVC matrix | 33% |

Figure 4A:
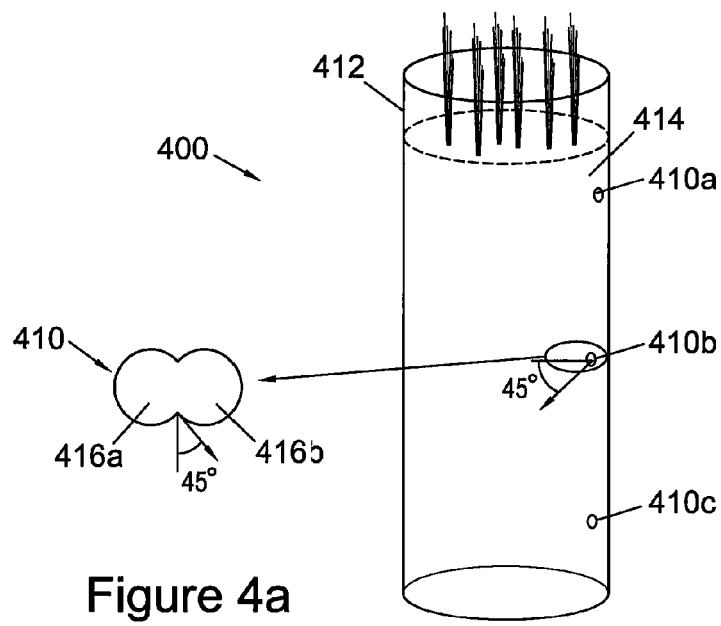
FIGS. 4a to 4c illustrate soil chemistry sensors in a soil column.
Figure 4B:
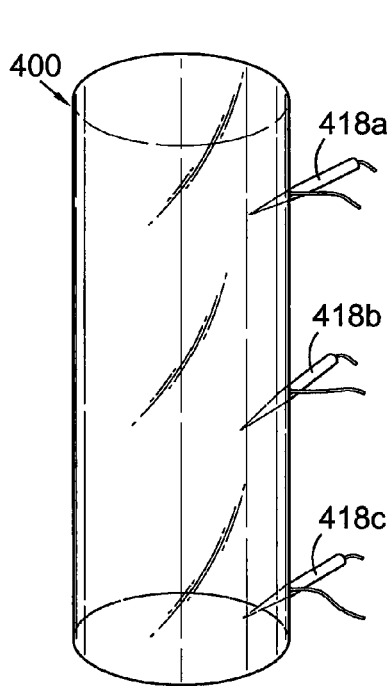
Figure 4C:
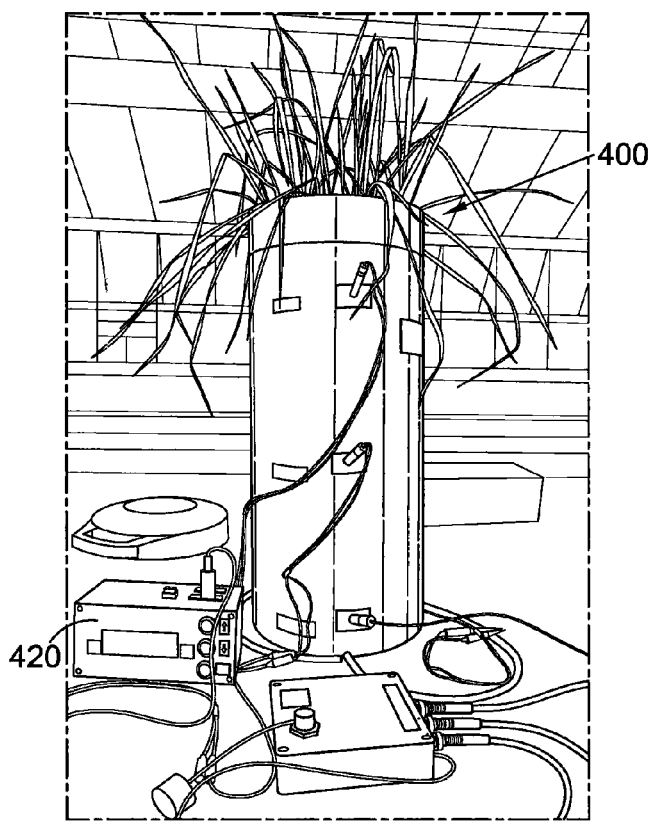

Use of Soil Chemistry Sensor to Detect Chemical Variation at Different Depths:

Turning now to FIGS. 4a to 4c, these illustrate a soil column system 400, according to an embodiment of the invention.

As shown in FIG. 4a, the soil column system 400 comprises a soil column 412 which is used to contain a volume of soil 414. One or more holes 410a, b, c are formed in the soil column 412 at different points along the length of the column. The one or more holes 410a, b, c are provided for one or more soil chemistry sensors. The soil column system enables the measurement of soil chemistry at different depths in the soil 414. Advantageously, this may enable determination of how chemicals move through soil (without any plants), and/or how chemicals are absorbed by plant root systems. For example, roots close to the top of the soil column 412 may absorb chemicals in the soil 414 at a different rate to those deeper in the soil column.

A soil sensor comprising a nitrate-selective electrode and a double junction reference electrode (as described above) is inserted into a hole 410 to enable measurement of the soil chemistry. In preferred embodiments, the soil column 412 comprises three holes 410a, b, c and a soil sensor is inserted into each hole to enable soil chemistry measurements to be taken at three depths, e.g. close to the top of the volume of soil 414 (i.e. for shallow/surface roots), mid-way along the length of the soil column 412 and close to the bottom of the volume of soil 414 (i.e. for deep roots). Preferably, the soil chemistry sensors are placed at 30 cm, 60 cm and 90 cm beneath the surface of the soil. As shown in FIG. 4a, hole 410 is adapted to the shape of the soil sensor electrodes, such that one electrode can be inserted into one part 416a of the hole, and the second electrode can be inserted into a second part 416b of the hole. Thus, the hole 410 substantially matches the size of the plastic lumen of the electrodes, to help to seal the hole and minimise any soil or soil water from leaking out of the hole 410.

FIG. 4b shows a soil column system 400 comprising three soil sensors 418a, b, c at three different positions along the soil column. FIG. 4c illustrates the soil column system 400 being used to measure soil chemistry at different depths. The silver/silver chloride electrode wires of each sensor are connected to a data logger and a high import impedance volt meter 420 (e.g. a differential electrometer).

Figure 5A:
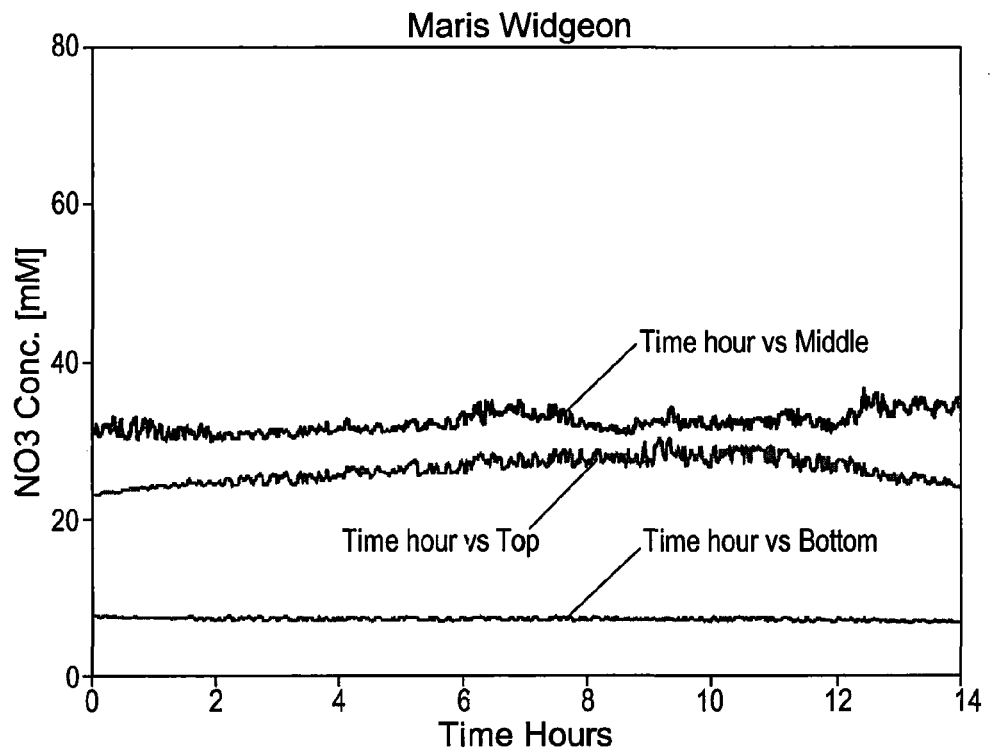
FIGS. 5a and 5b show soil nitrate data from measurements taken using the soil column of FIGS. 4a-c.
Figure 5B:
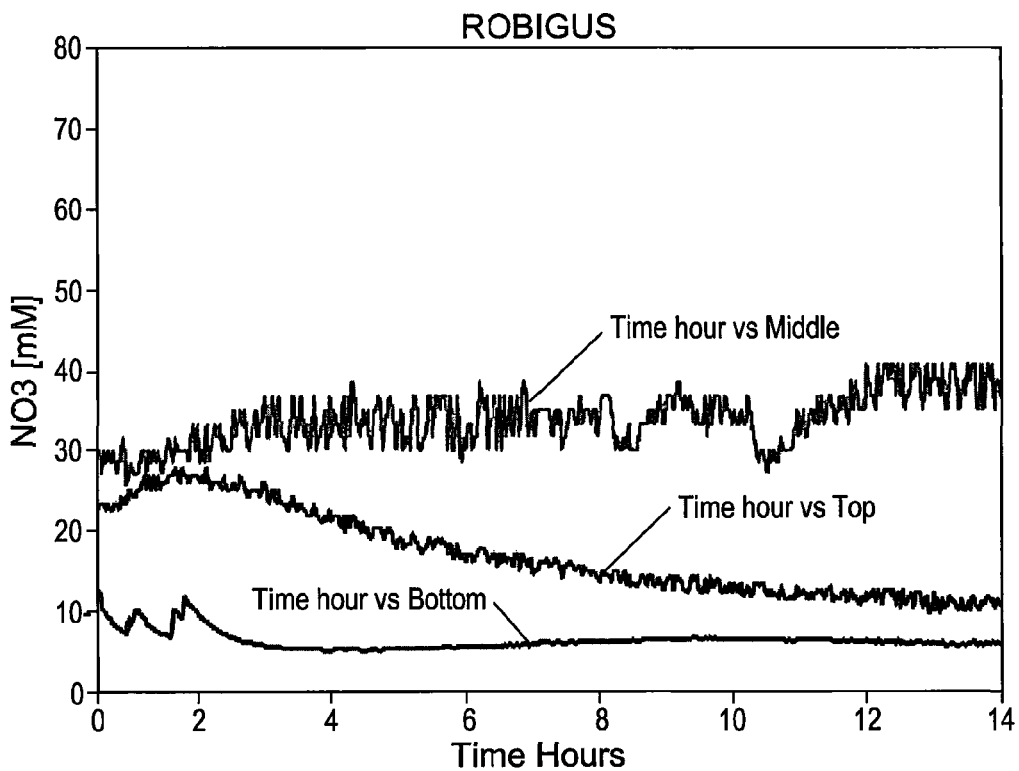

FIGS. 5a and 5b show soil nitrate data from measurements taken using the (three sensor) soil column system of FIGS. 4a-c. The soil column system was used to compare the nitrate uptake of two wheat cultivars: *Robigus*, which is known to have a high nitrate uptake efficiency, and *Maris Widgeon*, which is known to be have a low nitrate uptake efficiency. FIGS. 5a and 5b respectively depict the variation of nitrate depletion in the soil column over time at different depths in a column containing the *Maris* Widgeon, cultivar and in a column containing the *Robigus* cultivar. In both cases, soil nitrate concentrations were measured by the soil column system at three depths over a period of 14 hours. The soil column system not only verify the known nitrate uptake efficiency of the two cultivars, but advantageously also enables a better understanding of how the root systems of the two cultivars behave. For example, the locations of the soil nitrate sensors in the soil column system show that the roots of the *Robigus* wheat variety appear to absorb nitrates via their shallow roots (i.e. those at the top of the soil column). This may be useful information to wheat farmers, as it indicates that for particularly varieties of wheat, nitrate-rich fertilizer should be added frequently to the soil surface, whereas this may not be necessary for other varieties.

Thus, knowing the nitrate level at different depths in the soil/growth medium can help to optimise the amount of fertilizer to add to the soil to promote growth while also minimising leaching (i.e. loss of water-soluble nutrients from the soil). For example, a low nitrate concentration measured close to the top of the soil surface (e.g. 30 cm from the soil surface), may trigger the need for more fertilizer to be added. In particular, a trigger to add more fertilizer may be that the nitrate concentration 30 cm below the soil surface is, for example, 10-fold less than that at 60 cm or 90 cm below the soil surface. However, a high nitrate concentration (e.g. 5 times above the expected concentration of 15 mM) at 90 cm may also be indicative of leaching. Thus, the nitrate levels measured by the soil chemistry sensors may also be used to make decisions about irrigation. For example, if measurements indicate fertilizer needs to be added to the top of the soil, but that the soil is prone to leaching, then a farmer may use the information to decide when to irrigate after applying fertilizer to minimise the effect of the water washing away the nitrates from near the top of the soil surface.

Figure 6A:
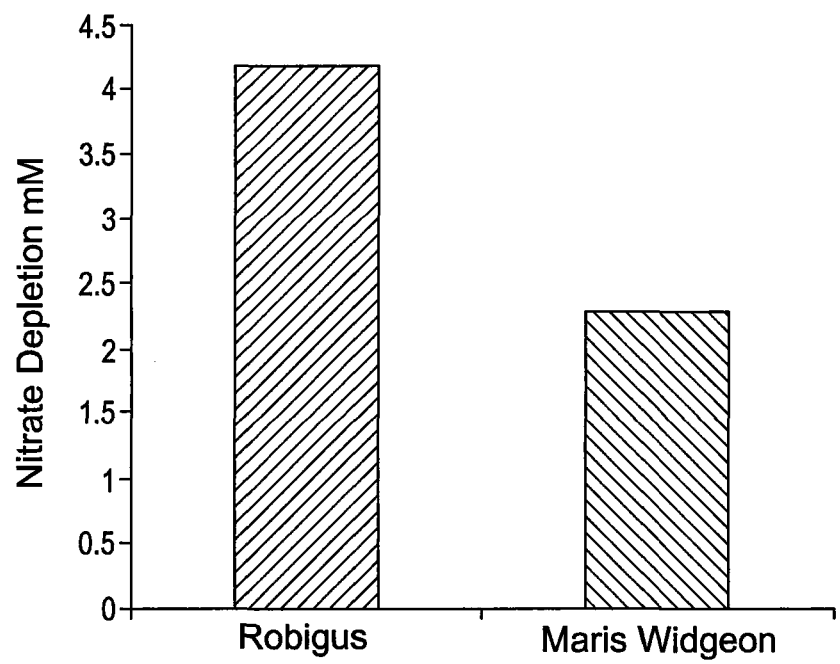
FIG. 6a shows soil nitrate depletion (uptake) data for two different cultivars.

Use of Soil Chemistry Sensor to Detect Chemical Variation in a Hydroponic Culture:

The above-described soil chemistry sensor may in embodiments be used to measure uptake of nutrients in a hydroponic growth culture. FIG. 6a shows nitrate depletion (uptake) data for two different cultivars in a hydroponic culture, i.e. a mineral nutrient solution (as opposed to in soil). In such embodiments, it is essential that the sensor is waterproof (except for the porous plugs), and the ion-sensing and reference electrodes may be sealed within a waterproof enclosure (for example, an enclosure fabricated from cold-shrink tubing).

Use of Soil Chemistry Sensor to Detect Chemical Variation in an Artificial Growth Medium:

In embodiments, the soil column system 400 shown in FIG. 4a may be adapted for a vermiculite growth medium and the soil chemistry sensors used to detect chemical variation in the vermiculite column at different depths. Typically, exfoliated vermiculite (a hydrous, silicate mineral), is combined with other materials such as peat or pine bark to form a soil-less growth media. Vermiculite-based media are known to promote faster root growth because the mixture helps retain air, plant food and moisture and releases them as the plant requires them. Thus, the vermiculite column system was used to determine how nitrates move through the profile of the artificial growth medium.

Figure 6B:
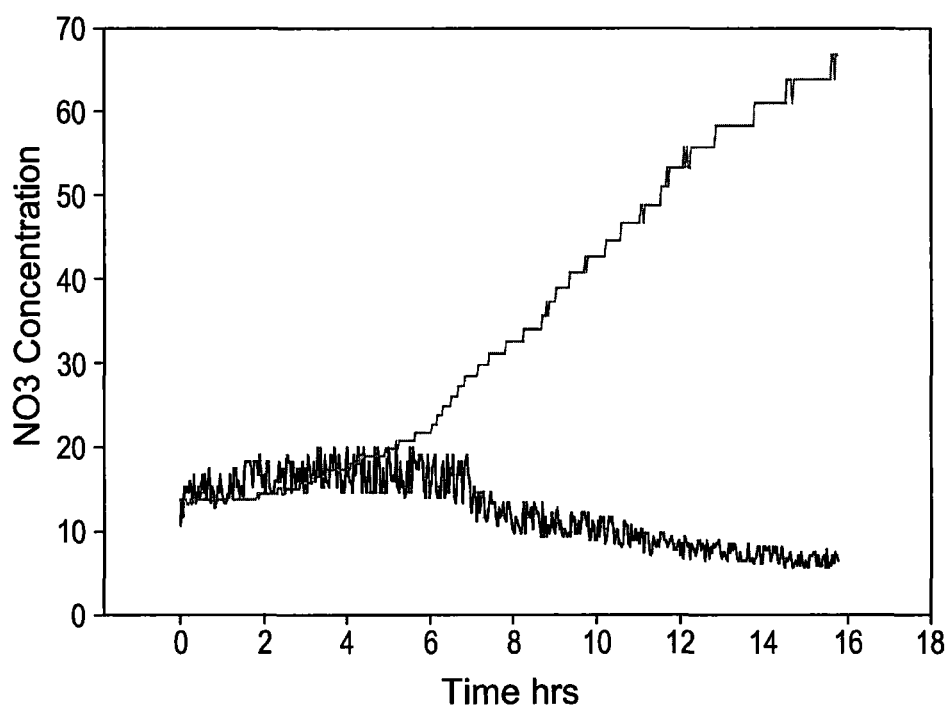
FIG. 6b shows a variation of nitrate concentration in a vermiculite column at two different column depths.

FIG. 6b shows a variation of nitrate concentration in a vermiculite column at two different column depths. The data was collected using a column without any plants in order to determine the change in nitrate concentration due to movement through the growth medium alone (i.e. without the effect of uptake by a plant). Nitrate was added to the top of the vermiculite column at time t=0. The data indicates that nitrates flow relatively quickly through the growth medium to reach the middle of the column.

Consequently, as described above, the soil chemistry sensor can be used to:

Provide measurements of soil chemistry rapidly, at a fine scale and in real time;

Measure chemical/nutrient uptake directly in hydroponic solutions;

Measure chemical (e.g. nitrate) depletion to predict chemical uptake by plants directly in soil at one or more depths;

Determine the effects of soil moisture gradients on chemical (e.g. nitrate) uptake;

Identify which fraction of root system is active in chemical uptake during a plant's developmental stages; and Determine the movement of nitrate through soil or a solid substrate (e.g. vermiculite) to determine leaching behaviour.

Use of Soil Chemistry Sensor to Measure Soil Chemistry Depletion Zones Around Plant Roots:

In embodiments, the above-described soil sensor may be used to identify 'depletion zones' around the roots of a plant. A nutrient depletion zone develops around a root when nutrients are removed from the soil solution faster than they can be replaced by the movement of nutrients through the solution. For example, ions which have low mobility in the solution may produce a sharp/narrow depletion zone close to the root.

Figure 7:
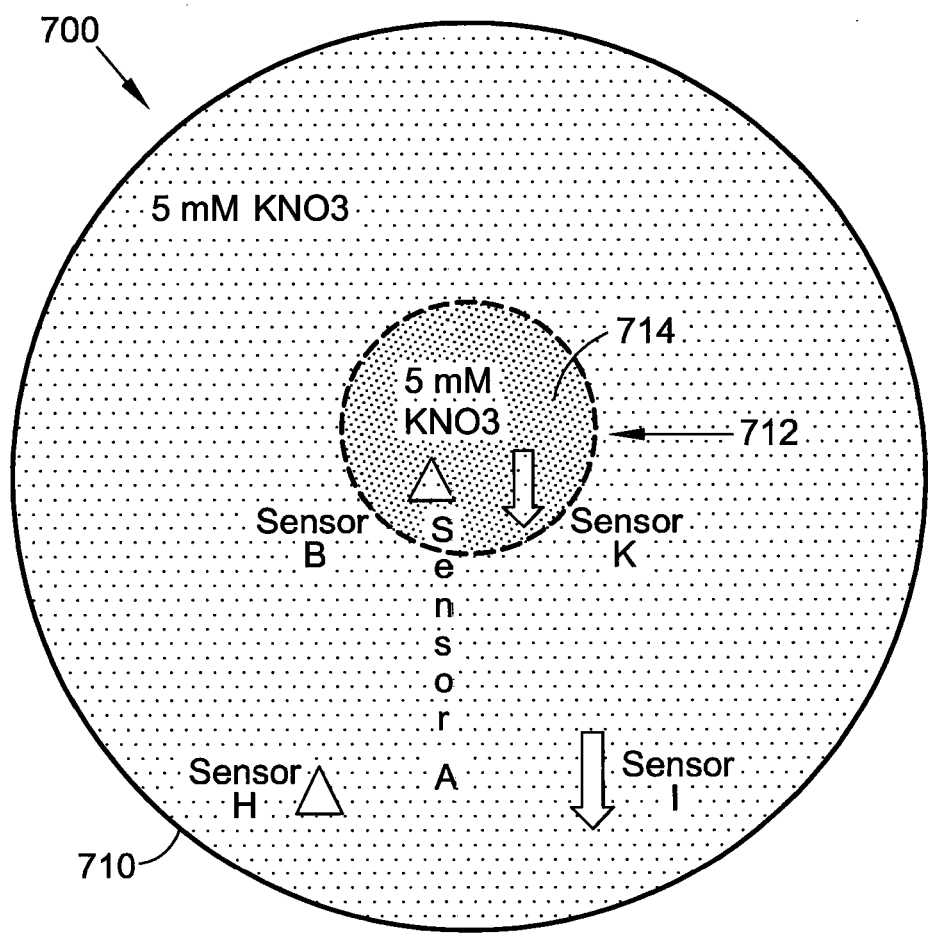
FIG. 7 shows a schematic of a soil chemistry sensor for measuring chemical depletion (uptake) around plant roots.

Turning now to FIG. 7, this depicts a schematic of a soil chemistry sensor for measuring chemical depletion (uptake) around plant roots, i.e. to identify a depletion zone around the roots. The depletion zone measuring apparatus 700 comprises a container 710 which contains the soil solution or growth medium. A single plant 714 is planted in the container 710. To measure nutrient uptake by the roots, the plant roots are contained within visking tubing 712. In the illustrated embodiment, two sensors are provided within the visking tubing 712, to measure changes in the nutrient levels close to the plant roots, and two sensors are provided in the container 710 away from the visking tubing 712, to measure changes in nutrient levels in the soil/growth medium away from the plant roots.

In an example embodiment, sensor B is placed 2 cm below the soil surface and sensor K is placed 6 cm below the soil surface, where both sensors B and K are provided within the visking tubing 712 (i.e. close to the roots). Further from the visking tubing/roots is sensor H, placed 2 cm below the soil surface, and sensor I, placed 6 cm below the soil surface. The four sensors together measure changes in the soil chemistry at two different depths in the container 710 and at two different distances away from the roots. The apparatus was used to measure soil chemistry changes and the depletion zone around wheat roots. The container 710 was filled with a sand culture with added nutrient solution as the growth medium.

Figure 8A:
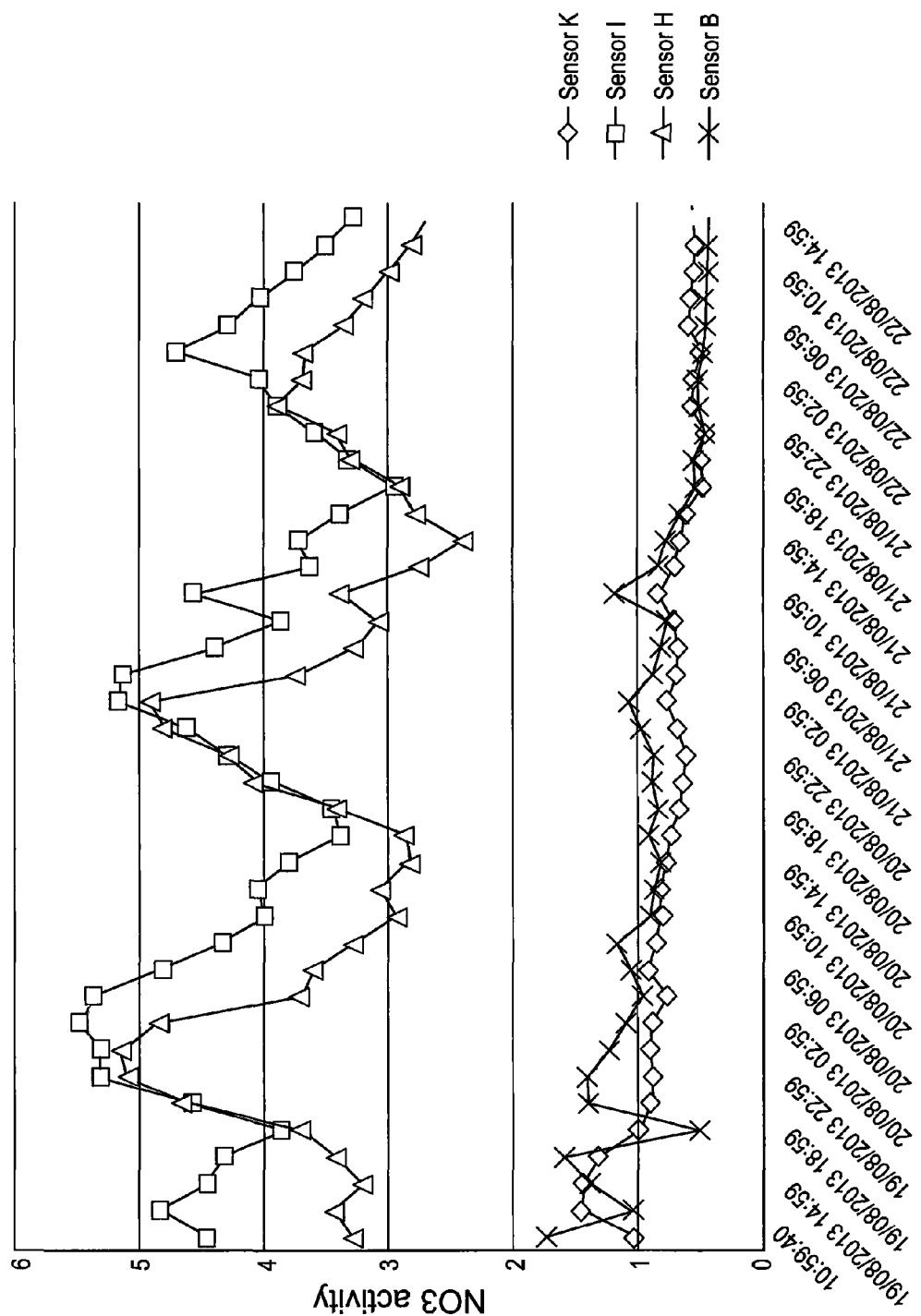
FIG. 8a shows a variation of soil nitrate depletion (uptake) over time at different points around plant roots.
Figure 8B:
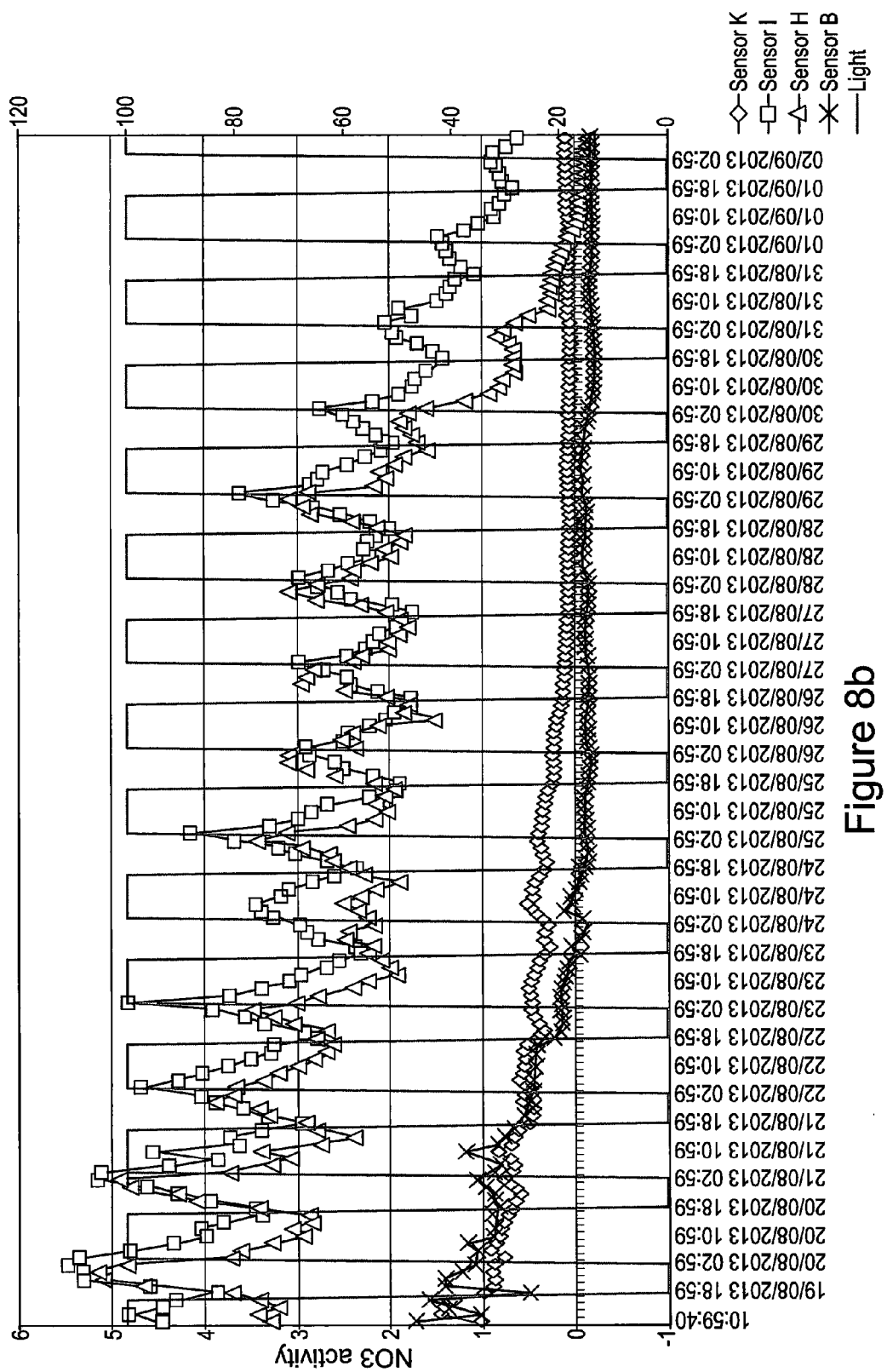
FIG. 8b shows a variation of soil nitrate depletion (uptake) over time at different points around plant roots, and a variation in light over time.

FIGS. 8a and 8b show respectively, data collected using this apparatus over a four day period and data collected over a fourteen day period. FIG. 8b also illustrates changes in light over the fourteen day period, which corresponds to the day/night cycle. The data shows that for this particular wheat variety, nitrates are absorbed by the roots at approximately the same rate at 2 cm and 6 cm below the surface of the soil. It also shows that as the nitrates are being depleted close to the roots, nutrients are drawn towards the roots through the visking tubing (i.e. nutrients are depleted around sensors H and I). Over fourteen days, the nitrates were depleted in the volume close to the plant roots. The nitrate concentration in the shallow culture further away from the roots was also depleted over this period. Such data can be used to estimate the depletion zone around plant roots, which may in this case be a few centimeters (e.g. 1 to 2 cm) from the surface of the roots.

Figure 9A:
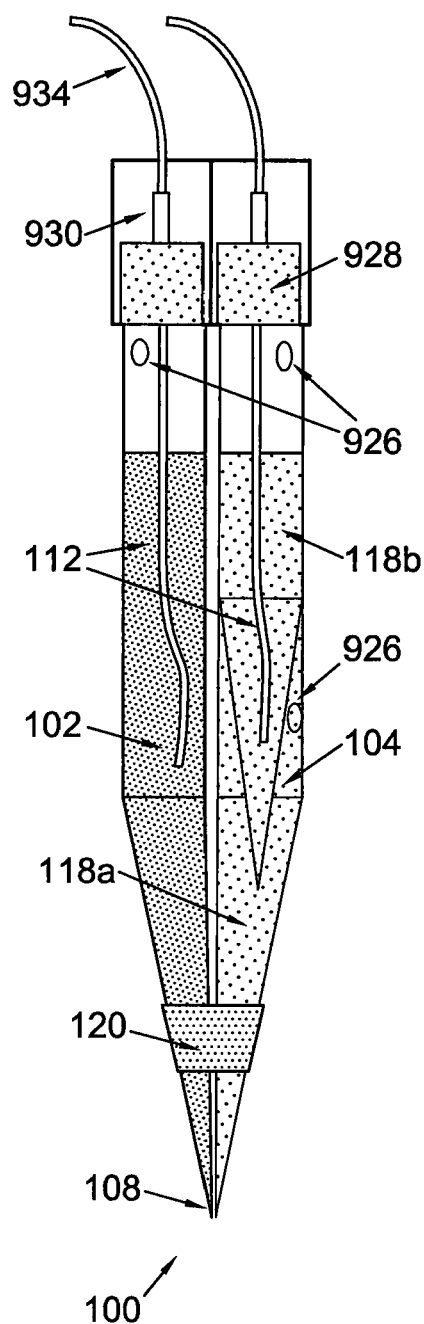
FIGS. 9a and 9b depict a soil chemistry sensor according to embodiments of the invention.

Consequently, the soil chemistry sensor can be used to:
Measure complete soil chemistry/nutrient depletion at the root surface;
Identify soil chemistry/nutrient depletion zones around the root; and
Measure diurnal changes in soil chemistry/nutrient depletion (nutrient uptake).
Electrode Design:

FIG. 9a shows a variation of the soil chemistry sensor of FIG. 1. In this embodiment, the soil chemistry sensor 100 further comprises one or more holes 926. The "breather holes" 926 are formed in the nitrate-selective electrode 102 and the double junction reference electrode 104, to equalise the pressure inside the electrodes 102 and 104 and outside the electrodes, particularly when being transported in a pressurised environment, such as on an aeroplane. The breather holes 926 may be greater than 1 mm in diameter. However, to minimise the risk of external matter (e.g. water/soil water) entering the sensors through the breather holes 926, the holes are preferably "pin holes" and <1 mm in diameter. Alternatively, breather holes 926 may be replaced with valves or taps to permit pressure equalisation and prevent external matter from entering the sensor. FIG. 9a also shows how the electrodes are sealed to prevent soil water from entering the electrodes through the top of the sensor 100. A plug 928, which may be formed of a pliable and/or water-resistant material, is inserted into the top of each electrode 102 and 104 around wires 112, to form a seal. In this embodiment, the ends of the electrode wires 112 are not encased in the sealant or the plugs 928, but rather a cable ferrule 930, such as a bootlace ferrule, is used to form an end termination of each wire 112. Thus, the cable ferrule 930 is not protected/insulated against any water that may leak through the top of the sensor 100. The coupling between the electrode wires 112 and a high import impedance volt meter (not shown) is provided by standard wire connections 934.

Figure 9B:
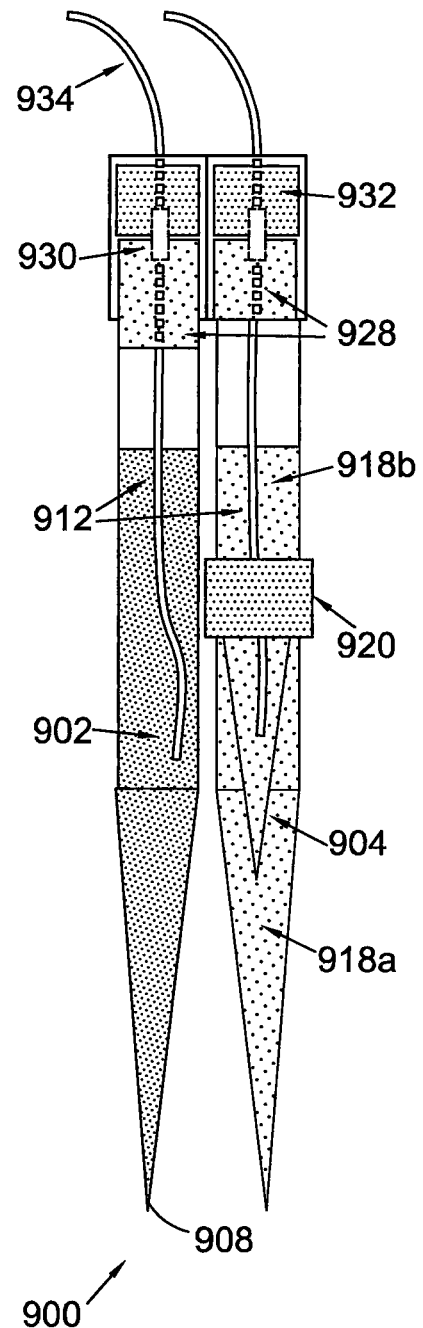

Turning now to FIG. 9b, this shows a further variation of the soil chemistry sensor of FIGS. 1 and 9a. The sensor 900 comprises a nitrate-selective electrode 902 and a double junction reference electrode 104, where the double junction reference electrode comprises different outer 918a and inner 918b filling solutions. Each electrode contains an electrode wire 912. As mentioned earlier, it is important to make the soil chemistry sensor waterproof (except for the porous plugs). Thus, preferably the ion-sensing and reference electrodes are sealed within a waterproof enclosure. In particular, top sealing the sensor is important to ensure that soil water does not get into contact with the circuitry of the sensor. In embodiments, the conducting wire of each electrode is passed through a plug 928 provided to seal the top of each electrode 902 and 904. Preferably, the plug 928 is plastic and/or formed from a pliable, water-resistant material, and forms a tight seal to prevent soil water from entering the electrode through the top end and protects the exposed conducting wire 112 from external environmental conditions. In the depicted embodiment, each cable ferrule 930 is partially encased in a plug 928 and an additional sealant 932 is disposed above plug 928 to provide a further seal and to protect cable ferrule 930 against water damage. The sealant 932 may be a putty-like water-repellent adhesive that can be pressed into each electrode to form a seal above the plug 928. Thus, no metal of each electrode is in contact with the soil/soil water in which the electrode is placed.

The soil chemistry sensor of FIG. 9b does not comprise "breather holes" as in the embodiment depicted in FIG. 9a. Advantageously, the lack of breather holes minimises the chance of the electrode solutions mixing with external water/soil water, which also prevents the chance of the sensor 900 short-circuiting.

A further sealant (not shown), e.g. a glue or adhesive material, may be used to strengthen the seal/s of the double-junction reference electrode 904 in order to prevent reference solution 918a, b from leaking out of their respective chambers. Preferably, rubber sleeving 920 is repositioned relative to the position of sleeving 120 shown in FIG. 9a, to further strengthen the double junction electrode 904.

Figure 9C:
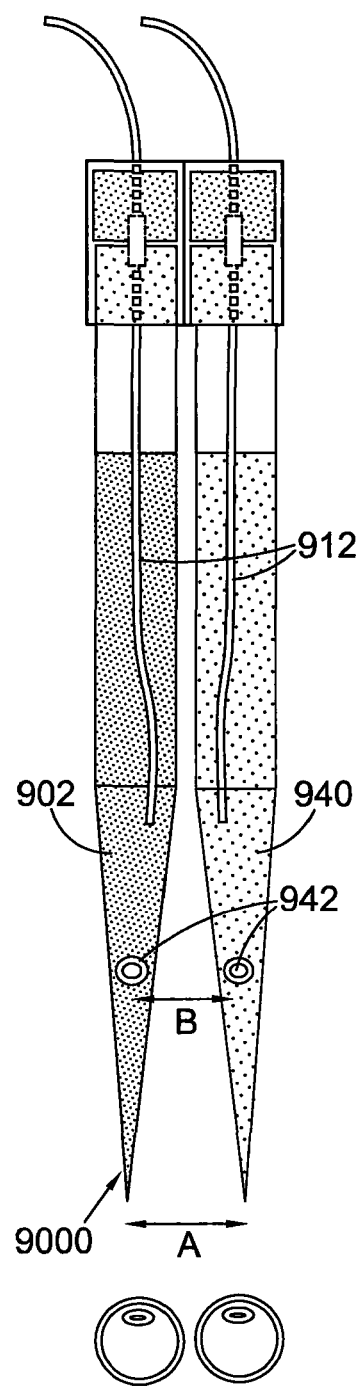
FIGS. 9c and 9d depict a soil chemistry sensor comprising side membranes according to an alternative embodiment of the invention.
Figure 9D:
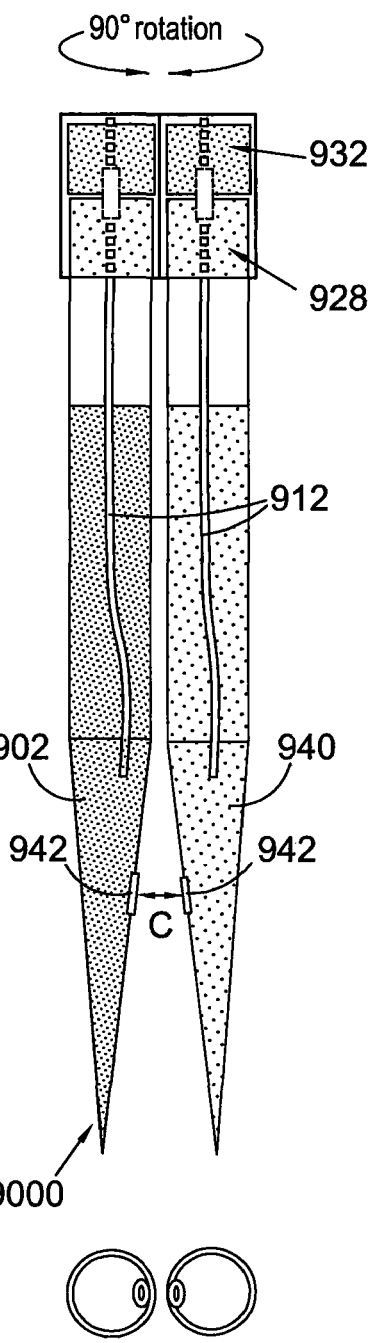

As described earlier with respect to FIG. 1, each electrode of the soil chemistry sensor 100 is fabricated from a pipette tip with a hole at the tip end to allow liquid to enter into and out of the pipette tip. Thus, the hole enables soil water and nutrients to contact the ion-selective/reference membrane and be sensed by the soil chemistry sensor. However, inserting the soil chemistry sensor vertically down into soil can damage the pipette tip and the membrane. An alternative embodiment is depicted in FIGS. 9c and 9d, which show a soil chemistry sensor 9000 comprising membranes 942 along a side of each pipette tip. Soil chemistry sensor 9000 is formed of an ion-selective electrode 902 and a single-tip reference electrode 940, where each electrode is formed of a pipette tip as described earlier. (Although not shown, the reference electrode 940 may be a double-junction reference electrode.) Holes are formed in the side of the pipette tip of each electrode and the ion-selective and reference membranes 942 are formed in the holes. Thus, even if the end of the pipette tip is damaged when the soil chemistry sensor is inserted into soil, the holes and membranes 942 will be undamaged and therefore the electrodes are not prevented from performing their sensing function.

As shown in FIG. 9d, preferably, the membrane 942 of each electrode is positioned such that the membranes face each other. This may require the electrodes 902 and 940 to be rotated from a side-by-side orientation, as shown in FIG. 9c, to a face-to-face orientation as shown in FIG. 9d. It is preferable that the electrodes 902 and 940 are close to each other (so that they each measure soil chemistry at approximately the same position in the soil structure) but are also insulated from each other to prevent shorting. Thus, as described above, the electrode wires 912 and any (metal) connectors (e.g. a cable ferrule) holding the wires in place are insulated by plug 928 and sealant 932, which also protects the wire and connectors from exposure to external conditions (e.g. soil water). In particular, the separation distance between the membranes of the electrodes 902 and 940 should be minimal, particularly when taking measurements in situ, as the soil structure and/or porosity may modify the water available for sensing by each of the electrodes. Thus, preferably the distance between the membranes is between 1-2 mm. More preferably, the distance (A) between the tips of each electrode is greater than the distance (B) between the membranes 942 when the membranes are side-by-side (as in FIG. 9c), and distance B is greater than the distance (C) when the membranes 942 are face-to-face (as in FIG. 9d), i.e. A>B>C.

Figure 9E:
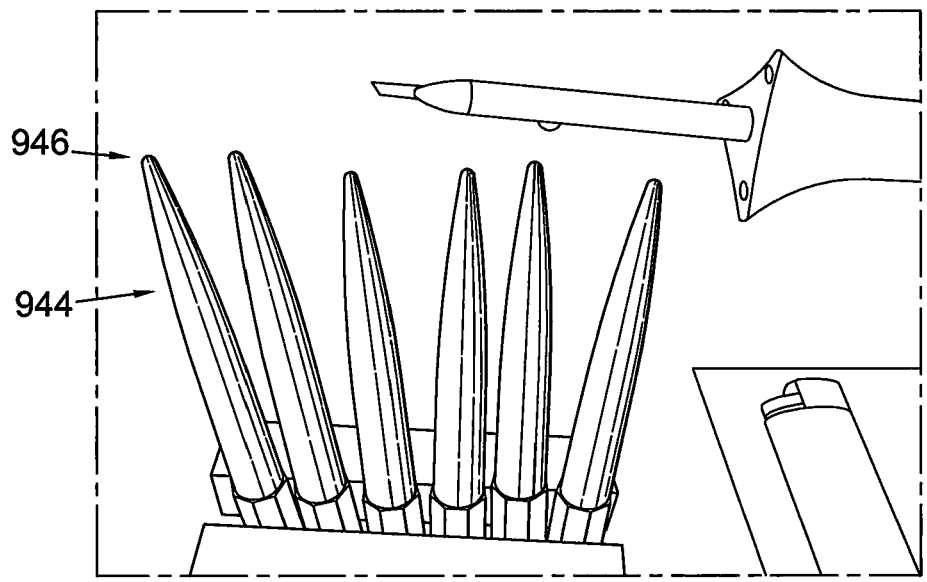
FIGS. 9e and 9f illustrate construction steps to form the side membranes of FIG. 9d.
Figure 9F:
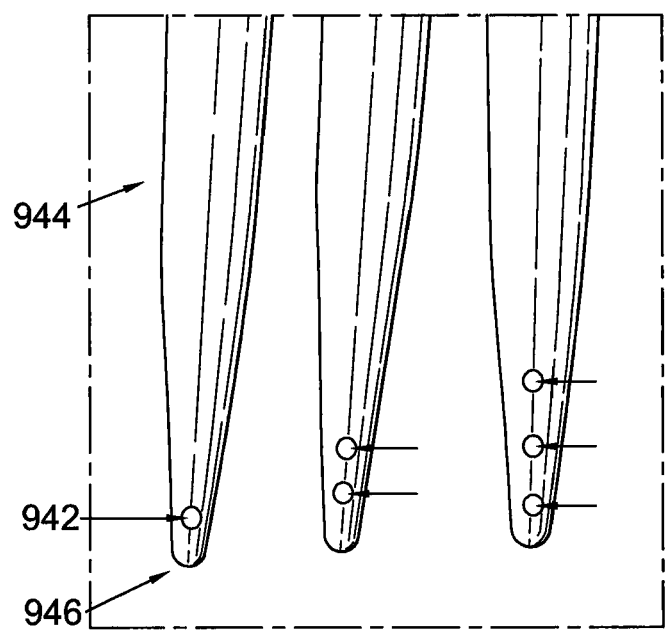

Turning now to FIGS. 9e and 9f, these depict the plastic lumen 944 of the side membrane soil chemistry sensor 9000 of FIG. 9d. As mentioned above, typically, a pipette tip 944 has a hole 946 at one end to allow liquid to enter into and out of the pipette tip. To form the side membranes of the soil chemistry sensor 9000, the hole 946 of each pipette tip is sealed using a soldering iron and one or more holes 942 are formed along the length of the pipette tip instead. The holes may be formed using a hot needle that is inserted into the pipette tip 944 at desired locations. The membrane is formed as described earlier.

In embodiments, the soil chemistry sensor 9000 of FIGS. 9c and 9d may be covered in a plastic or water-resistant material to provide an insulating and water-proof layer over the sensor 9000. Techniques such as plasti-dip may be used to provide the layer. Preferably, the layer covers all but the membranes of the electrodes.

Figure 9G:
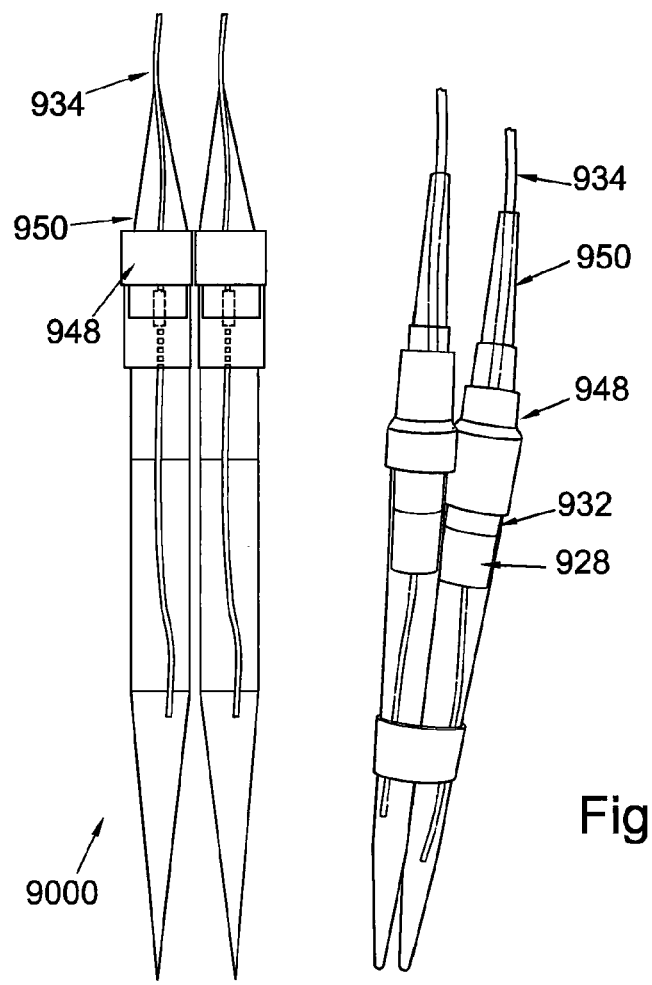
FIGS. 9g and 9h illustrate construction steps to seal the soil chemistry sensor of FIG. 9d.
Figure 9H:
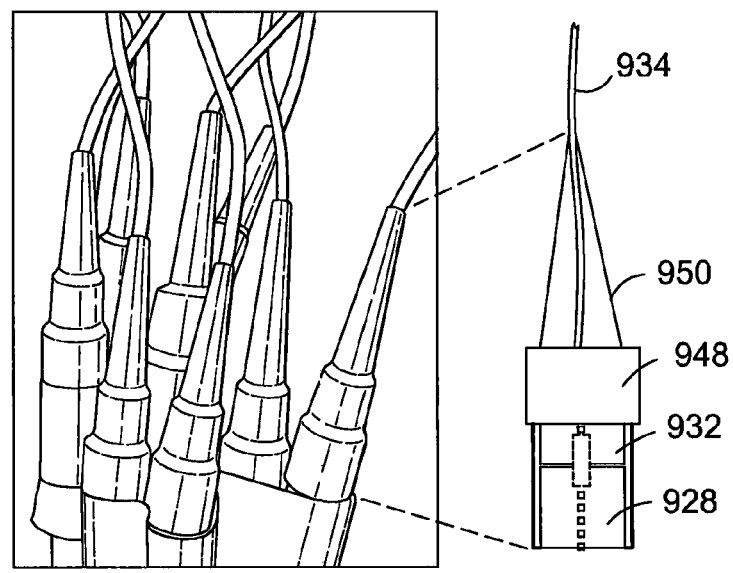

In embodiments, the soil chemistry sensor 9000 may be formed with an additional protective cover over the wires extending from out of the electrodes. As shown in FIGS. 9g and 9h, a pipette tip 950 is attached to the electrodes such that the wide end contacts the sealant 932 and the connecting wire 934 is passed through the narrow end/tip of the pipette tip 950. The pipette tip 950 prevents the connections between the electrode wire and the connecting wire 934 from damage. A protective rubber sleeving 948 is provided over the pipette tip 950 to secure the pipette in position and to provide a degree of flexibility to the connection between the electrode and wire 934. A plastic coating, as shown in FIG. 9h, may be provided over the pipette tip 950 to provide an insulating and water-proof layer over the connection. The plastic coating may be formed by the plasti-dip technique or otherwise.

As described above, each of the ion-selective and reference electrodes is fabricated from a plastic lumen, which in embodiments is formed of a disposable pipette tip for low cost. Another advantage to using a disposable pipette tip over a plastic syringe is that the small pipette tip ensures a smaller surface area of the ion-selective membrane is in contact with the soil water, and thus, the risk of damage to the membrane is reduced.

Measuring Soil Chemistry In Situ at Different Depths with Vertical Sensors

The soil chemistry sensors described thus far are capable of measuring the soil chemistry in situ at a certain distance below the surface of the soil, where the distance itself (i.e. depth) is limited by the length of sensor/sensor electrodes. The soil column system shown in FIG. 4a is suitable for measuring soil chemistry within the soil column, i.e. for a plant grown within the column, but is not suitable for in situ measurements (e.g. in a field). It may be desirable to measure the soil chemistry deeper in a soil structure in a field, and/or to measure the soil chemistry at multiple different depths in a soil structure simultaneously, and/or to obtain real-time soil chemistry data in situ. If real-time measurements indicate that fertilizer needs to be added to the top of the soil, but that the soil is prone to leaching, then a farmer may use the information to decide when to irrigate after applying fertilizer to his crops to minimise the effect of the water washing away the nitrates from near the top of the soil surface.

Figure 10A:
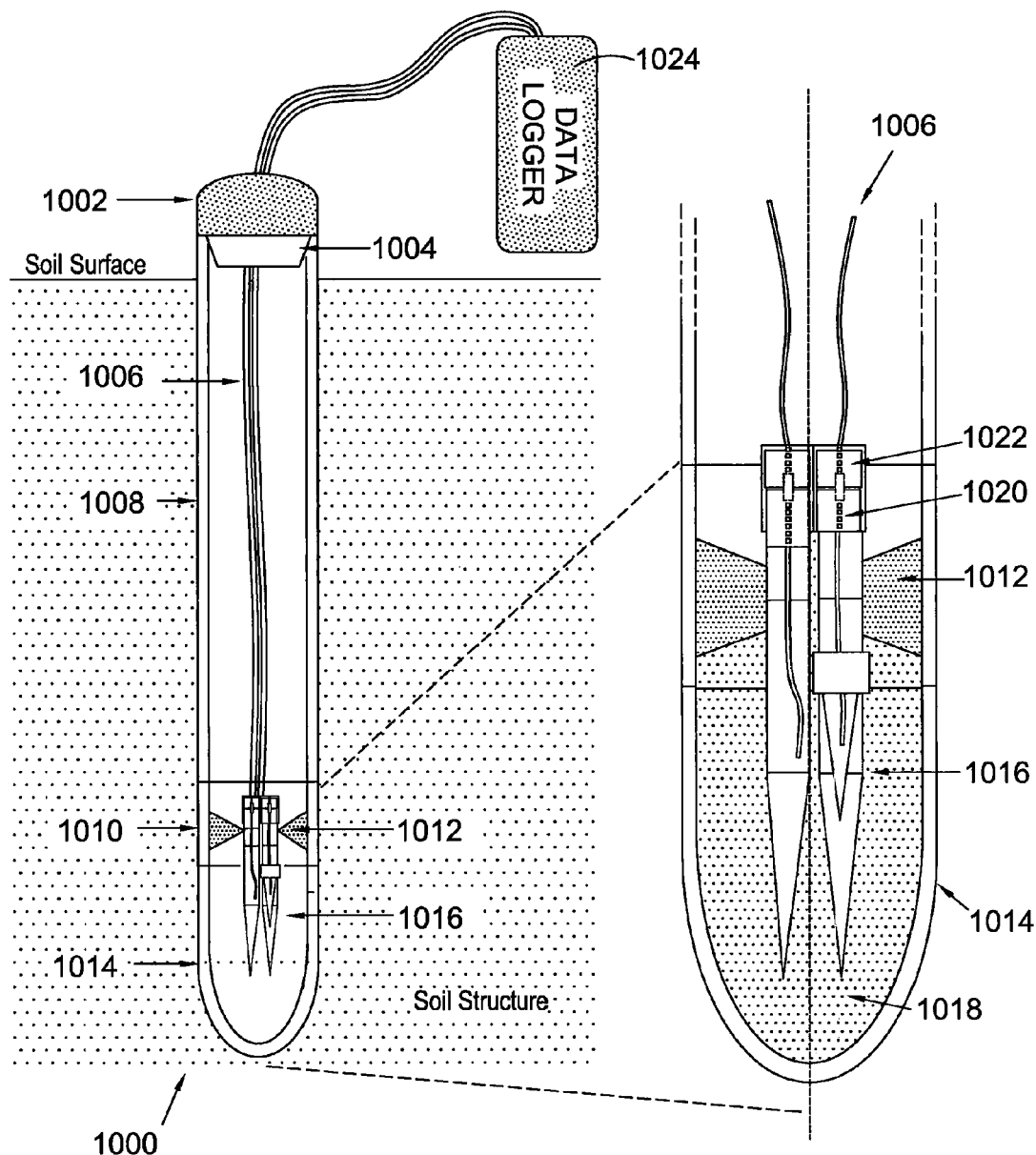
FIG. 10a shows a probe comprising a vertical soil chemistry sensor for measuring soil chemistry within a soil structure, according to an embodiment of the invention.

FIG. 10a shows a variable length probe 1000 comprising a vertical soil chemistry sensor for measuring soil chemistry within a soil structure, according to an embodiment of the invention. The soil chemistry sensor 1016 is substantially similar to that shown in FIG. 9b, and comprises an ion-selective electrode, a double-junction reference electrode, a plug 1020 and sealant 1022 to seal each electrode. The probe 1000 is formed of three main parts: a non-porous tube part 1008, an adaptor part 1010, and a porous cap part 1014. The non-porous tube part 1008 is provided by a tube or pipe of a length required to place the soil chemistry sensor at a particular depth below the soil surface. Thus, advantageously, the probe 1000 has an adjustable length, which is adjusted by constructing the probe from a non-porous tube part 1008 of the length required to place the sensor at the required depth. The tube part 1008 may be provided by an insulating and water-proof material, e.g. a plastic tube/pipe, to protect the top of the soil sensor 1016 and electrical wiring 1006 from contact with the external environment (e.g. water/soil water). Porous cap part 1014 is formed of a porous material, e.g. ceramic, to enable soil water to enter the probe 1000 for sensing by the soil chemistry sensor 1016 contained with the probe 1000. As shown in more detail in the zoomed-in view of the sensor-end of probe 1000, the porous cap part 1014 contains a liquid (water) reservoir 1018. Electrolytes/ions in the soil outside of the porous cap part 1014 flow into the reservoir 1018, enabling the soil chemistry sensor 1016 to measure the soil chemistry via the reservoir 1018 rather than by direct contact with the soil.

Adaptor part 1010 couples together the non-porous tube part 1008 and the porous cap part 1014. In addition, adaptor 1010 secures the soil chemistry sensor 1016 in a vertical position within the cap part 1014. A circular gasket 1012 within the adaptor 1010 both holds the soil chemistry sensor 1016 in place within the cap part 1014 and forms a water-tight seal to prevent fluid in the reservoir 1018 from leaking out of cap part 1014 and into contact with the wiring 1006 in the tube part 1008. Preferably, gasket 1012 is formed of a water-resistant material such as rubber.

As shown in FIG. 10a, the probe 1000 is inserted into the soil structure so that the sensor end of the probe is at the desired depth at which the measurements are to be taken. The probe 1000 is sealed at the top end with a rubber stopper 1004 and a plastic cap 1002 to prevent water/external matter from entering the tube part 1008 and contacting the wiring 1006. Wiring 1006 is fed through the stopper 1004 and cap 1002 to connect the electrodes to a data logger 1024.

Figures 10B, 10C:
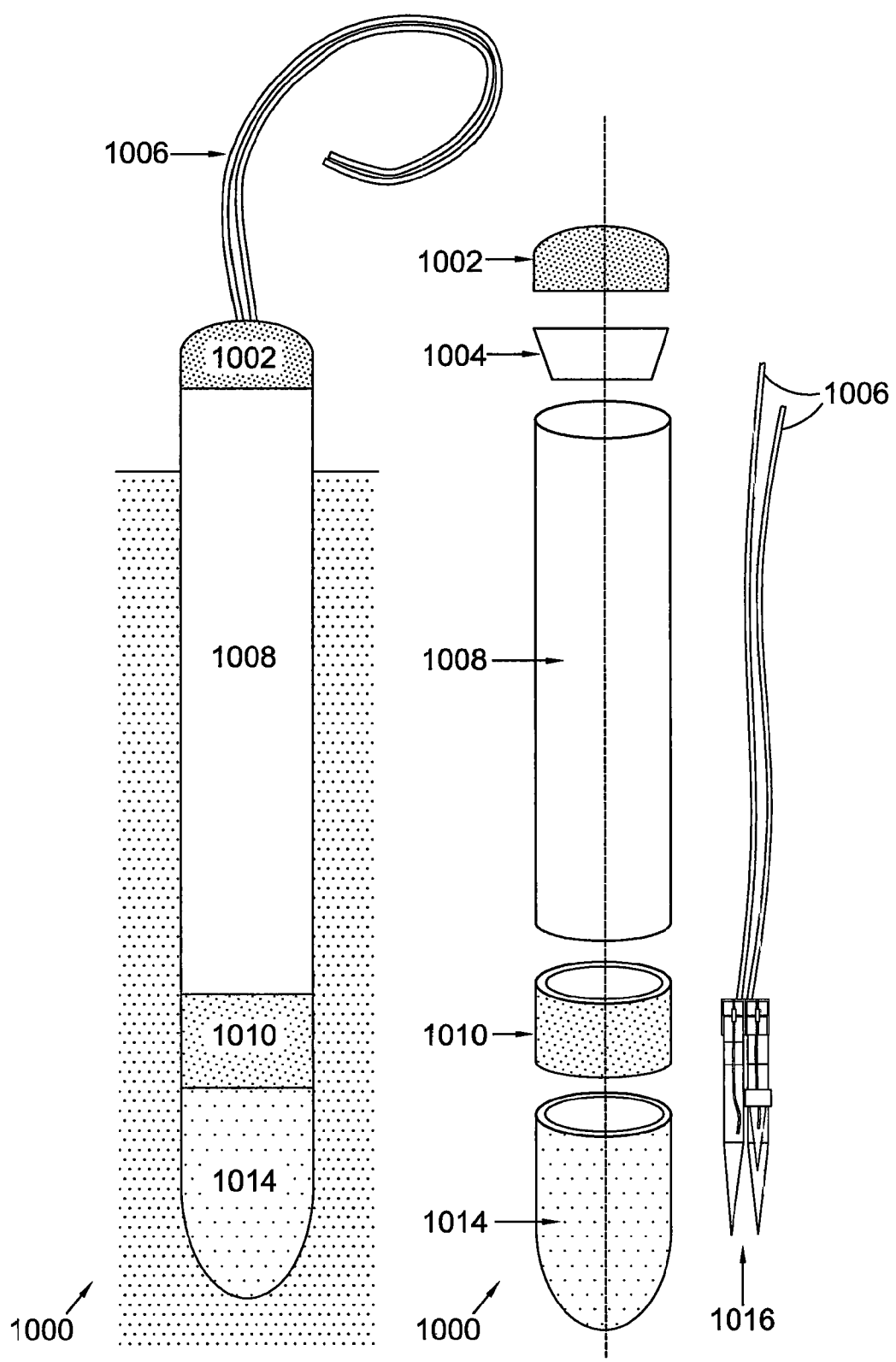

FIGS. 10b and 10c show external views of the probe of FIG. 10a, and in particular show the three main parts of probe 1000. The porous part 1014 may be detachably coupled to adaptor part 1010 by, for example, a threaded connection (not shown). Similarly, adaptor part 1010 may be detachably coupled to tube part 1008. Consequently, as mentioned above, the length of the probe 1000 may be altered by selecting a tube part 1008 of a particular length (or by changing the length of the adaptor part 1010 or porous cap part 1014). A further advantage of probe 1000 is that the soil chemistry sensor 1016 can be readily removed from the probe 1000 if the sensor is not functioning and/or to change the ion-selective electrode to measure the presence of different chemicals in the soil.

Figure 10D:
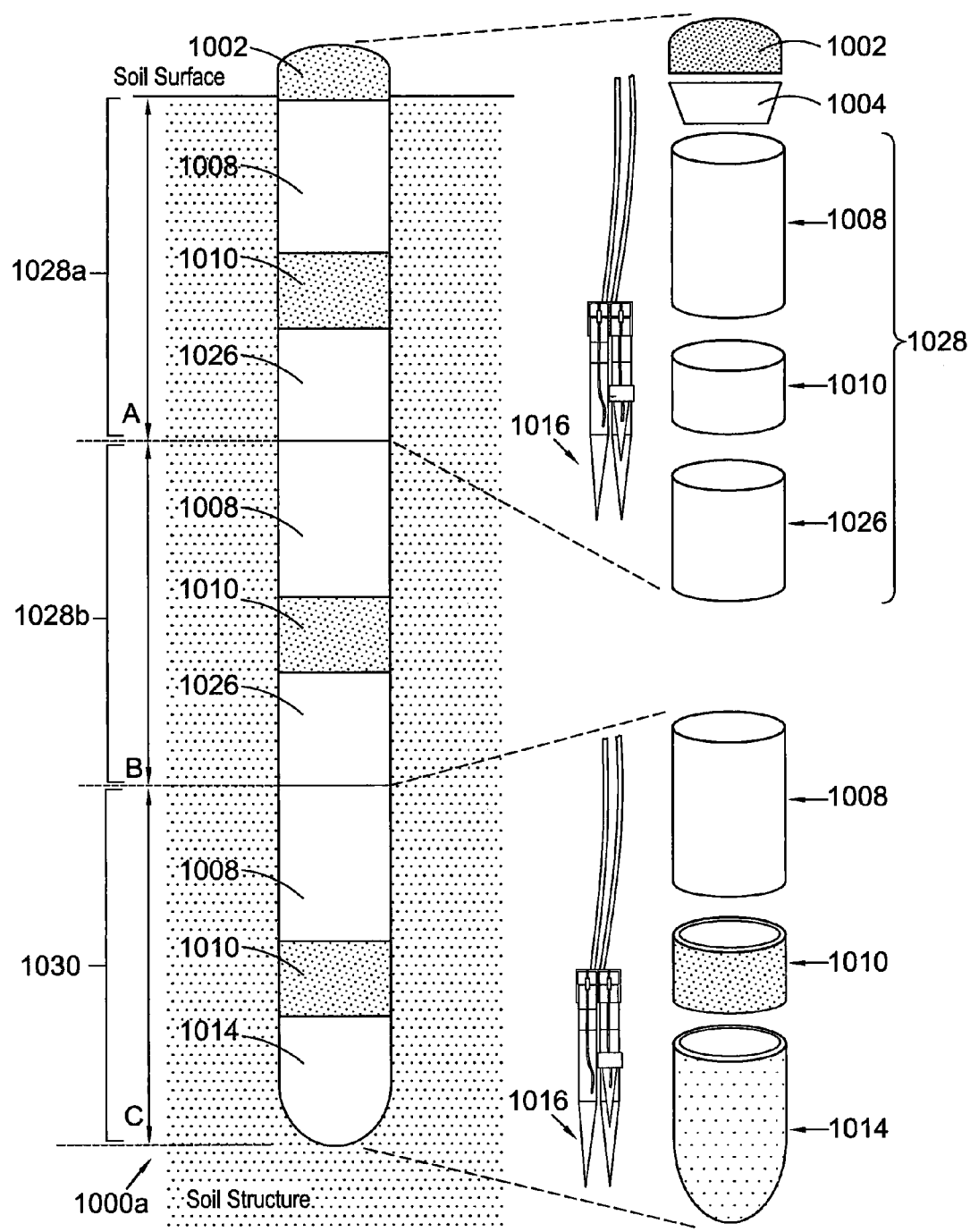
FIG. 10d shows a probe comprising multiple vertical soil chemistry sensors for measuring soil chemistry at multiple depths within a soil structure, according to an embodiment of the invention.

Turning now to FIG. 10d, this shows a probe 1000a which comprises multiple vertical soil chemistry sensors, for measuring soil chemistry at multiple depths within a soil structure, according to an embodiment of the invention. In this embodiment, probe 1000a comprises one or more sensor sections 1028 and a tip sensor section 1030. Each sensor section 1028 comprises a non-porous tube part 1008, an adaptor part 1010 and a porous part 1026. The tip sensor section 1030 comprises a non-porous tube part 1008, an adaptor part 1010 and a porous cap part 1014. The length of each sensor section 1028 and the tip sensor section 1030 is alterable (by, for example, altering the length of tube part 1008 as described earlier), to take soil chemistry measurements at two or more desired depths in the soil structure below the soil surface. The porous part 1026 may be detachably coupled to adaptor part 1010 by, for example, a threaded connection (not shown). Similarly, adaptor part 1010 may be detachably coupled to tube part 1008. Consequently, as mentioned above, the length of the probe 1000 may be altered by selecting a tube part 1008 of a particular length (or by changing the length of the adaptor part 1010 or porous cap part 1026).

One or more sensor sections 1028 may be detachably coupled together to form probe 1000a, such that the porous part 1026 of one sensor section 1028 is coupled to the tube part 1008 of an adjacent sensor section 1028. For example, the probe 1000a illustrated in FIG. 10d is capable of measuring soil chemistry at three different depths below the soil surface. Thus, the probe is formed of two sensor sections 1028a, b and a tip sensor section 1030. The first sensor section 1028a is used to sense soil chemistry at a depth A in the soil structure. As shown, the tube portion 1008 of the first sensor section 1028a is sealed using a rubber stopper 1004 and plastic cap 1002 to prevent water/soil water from entering probe 1000a from the top of the probe. The porous part 1026 of the first sensor section 1028a is coupled to the tube part 1008 of the second sensor section 1028b. The second sensor section 1028b is capable of measuring soil chemistry at a depth B in the soil structure. The porous part 1026 of second sensor section 1028b is coupled to the tube part 1008 of tip sensor section 1030. The tip sensor section 1030 is capable of measuring soil chemistry at a depth C in the soil structure. The porous cap part 1014 of the tip sensor section 1030 forms the tip of probe 1000a (i.e. no sensor sections can be coupled to the porous cap part 1014).

As described earlier with reference to FIG. 10a, each soil chemistry sensor 1016 of each sensor section 1028, 1030 is held by adaptor 1010 such that the ion-selective and reference membranes are immersed in a liquid reservoir contained within each porous part 1026 and 1014. Each porous part 1026 is fabricated such that electrical wires from each sensor 1016 can pass through the porous part 1026 and extend out through the top of sensor 1000a. In addition, each porous part 1026 is fabricated to minimise the risk of the liquid reservoir within each porous part 1026 leaking out into adjacent sensor sections. Consequently, the electrical wires may be covered with an insulating and water-proof material to prevent shorting.

Measuring Soil Chemistry In Situ at Different Depths with Horizontal Sensors

Figure 11A:
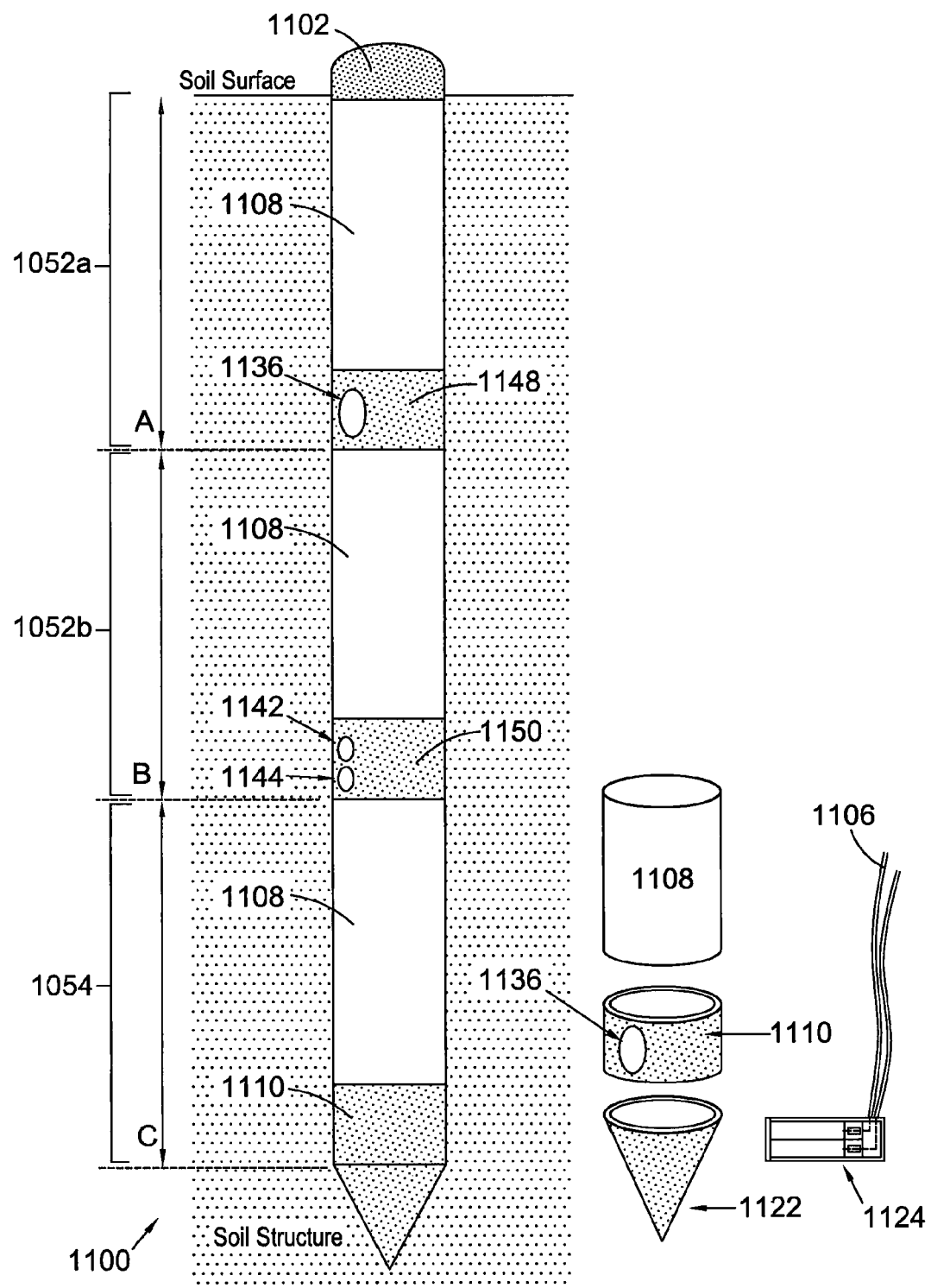
FIG. 11a shows a probe comprising multiple horizontal soil chemistry sensors for measuring soil chemistry at multiple depths within a soil structure, according to an alternative embodiment of the invention.

FIG. 11a shows a probe 1100 comprising multiple horizontal soil chemistry sensors for measuring soil chemistry in situ at multiple depths within a soil structure, according to an alternative embodiment of the invention.

In this embodiment, probe 1100 comprises one or more sensor sections 1152 and a tip sensor section 1154. Each sensor section 1152 comprises a non-porous tube part 1108 and a sensor part 1148 or 1150. The tip sensor section 1154 comprises a non-porous tube part 1008, a sensor part 1110 and a pointed tip 1122. The length of each sensor section 1152 and the tip sensor section 1154 is adjustable (by, for example, selecting tube part 1108 with different lengths as described earlier), to take soil chemistry measurements at two or more desired depths in the soil structure below the soil surface. The sensor part 1148 or 1150 may be detachably coupled to tube part 1108 by, for example, a threaded connection (not shown).

One or more sensor sections 1152 may be detachably coupled together to form probe 1100, such that the porous part of one sensor section 1152 is coupled to the tube part 1108 of an adjacent sensor section 1152. For example, the probe 1100 illustrated in FIG. 11a is capable of measuring soil chemistry at three different depths below the soil surface. Thus, the probe 1100 is formed of two sensor sections 1152a, b and a tip sensor section 1154. The first sensor section 1152a is used to sense soil chemistry at a depth A in the soil structure. As shown, the tube portion 1108 of the first sensor section 1154a is sealed by a rubber stopper (not shown) and a plastic cap 1102 to prevent water/soil water from entering probe 1100 from the top. The sensor part 1148 or 1150 (described in more detail below) of the first sensor section 1152a is coupled to the tube part 1108 of the second sensor section 1152b. The second sensor section 1152b is capable of measuring soil chemistry at a depth B in the soil structure. The sensor part 1150 or 1148 of second sensor section 1152b is coupled to the tube part 1108 of tip sensor section 1154. The tip sensor section 1154 is capable of measuring soil chemistry at a depth C in the soil structure. The pointed tip 1122 of the tip sensor section 1154 forms the tip of probe 1100. The pointed tip 1122 is preferably a sharp metal tip which helps insertion of the probe 1100 into a soil structure, and minimises damage to the end of probe 1100 and the sensors inside the probe.

Figure 11B:
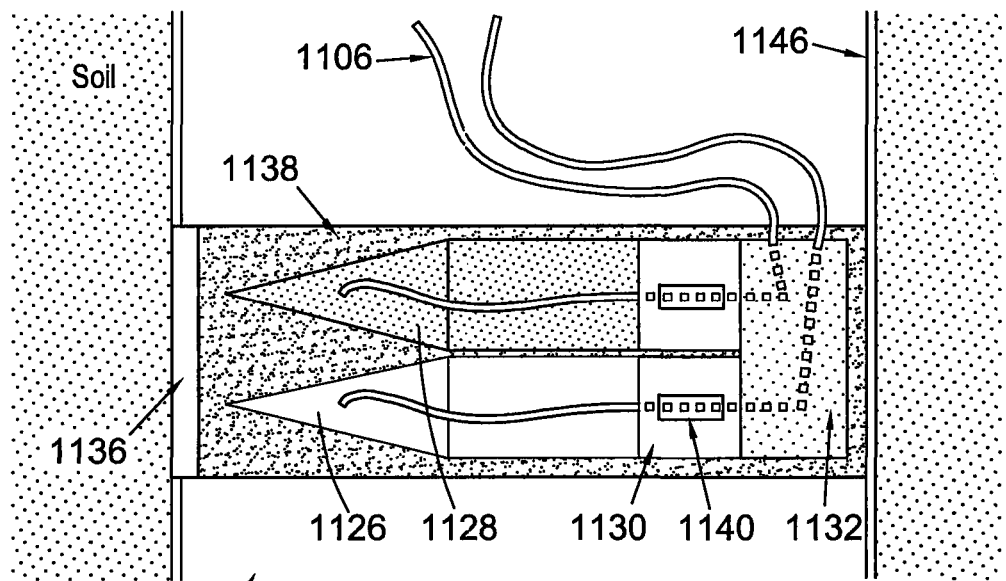
Figure 11C:
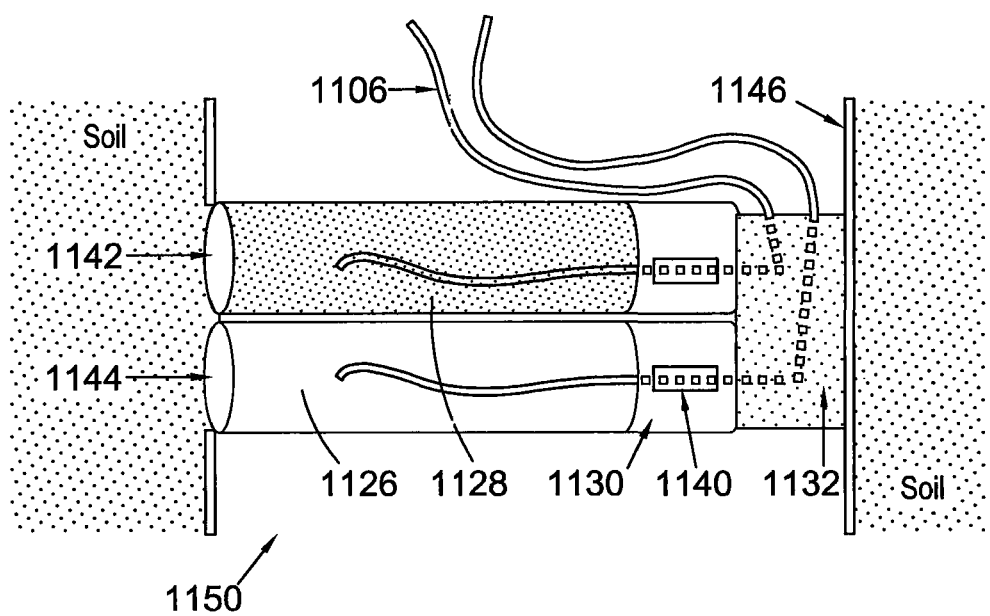

As shown in FIG. 11a, a soil chemistry sensor 1124 is located within each sensor part in a substantially horizontal/lateral orientation. Turning now to FIGS. 11b and 11c, these depict in more detail two different arrangements for the horizontal soil chemistry sensors 1124. Probe 1100 may be formed using either or each of the sensor parts 1148, 1150 described below.

FIG. 11b shows sensor part 1148, which comprises a porous membrane 1136 and a soil chemistry sensor 1124. The sensor part 1148 contains a liquid (water) reservoir 1138. Electrolytes/ions in the soil directly outside of the membrane 1136 flow into the reservoir 1138 though porous membrane 1136, enabling the soil chemistry sensor 1124 to measure the soil chemistry via the reservoir rather than by direct contact with the soil. The sensor part 1148 is tightly sealed to prevent the liquid in the reservoir 1138 from leaking into an adjacent sensor section. Wiring 1106 from each ion-selective electrode 1126 and reference electrode 1128 exits each sensor part 1148 through a tight seal (not shown) to prevent leakage. In embodiments, the sensor part 1148 (and 1150) may not extend across the full width or cross-section of the probe 1100, such that wiring 1106 from each electrode may run up through the probe 1100 in a space not occupied by the sensor parts.

FIG. 11c shows sensor part 1150 in more detail, which comprises a 'button-shaped' membrane 1142 on reference electrode 1128 and a 'button-shaped' membrane 1144 on ion-selective electrode 1126. Here, electrodes 1128 and 1126 may not be formed fabricated using pipette tips as described above. The membranes 1142 and 1144 are flush or substantially flush with the surface of probe 1100. In this arrangement, sensor part 1150 does not require a liquid reservoir, as the membranes of the electrodes are in direct contact with the external environment (e.g. soil or water). Advantageously therefore, the sensing membranes 1142 and 1144 sense chemical concentrations in the soil adjacent each membrane, rather than merely the chemicals which flow into a liquid reservoir. This may be particularly preferable when the probe 1100 is used to measure the chemistry of soil water, which flows slowly through a soil structure. The embodiment shown in FIG. 11*b* may be preferred when measuring chemical concentrations in water (e.g. hydroponic growth media or rivers). As above, the sensor part 1150 may not extend across the full width or cross-section of probe 1100, such that wiring 1106 which connects the electrodes to a data logger (not shown) may run up through the probe 1100 in a space not occupied by the sensor parts.

Figure 12A:
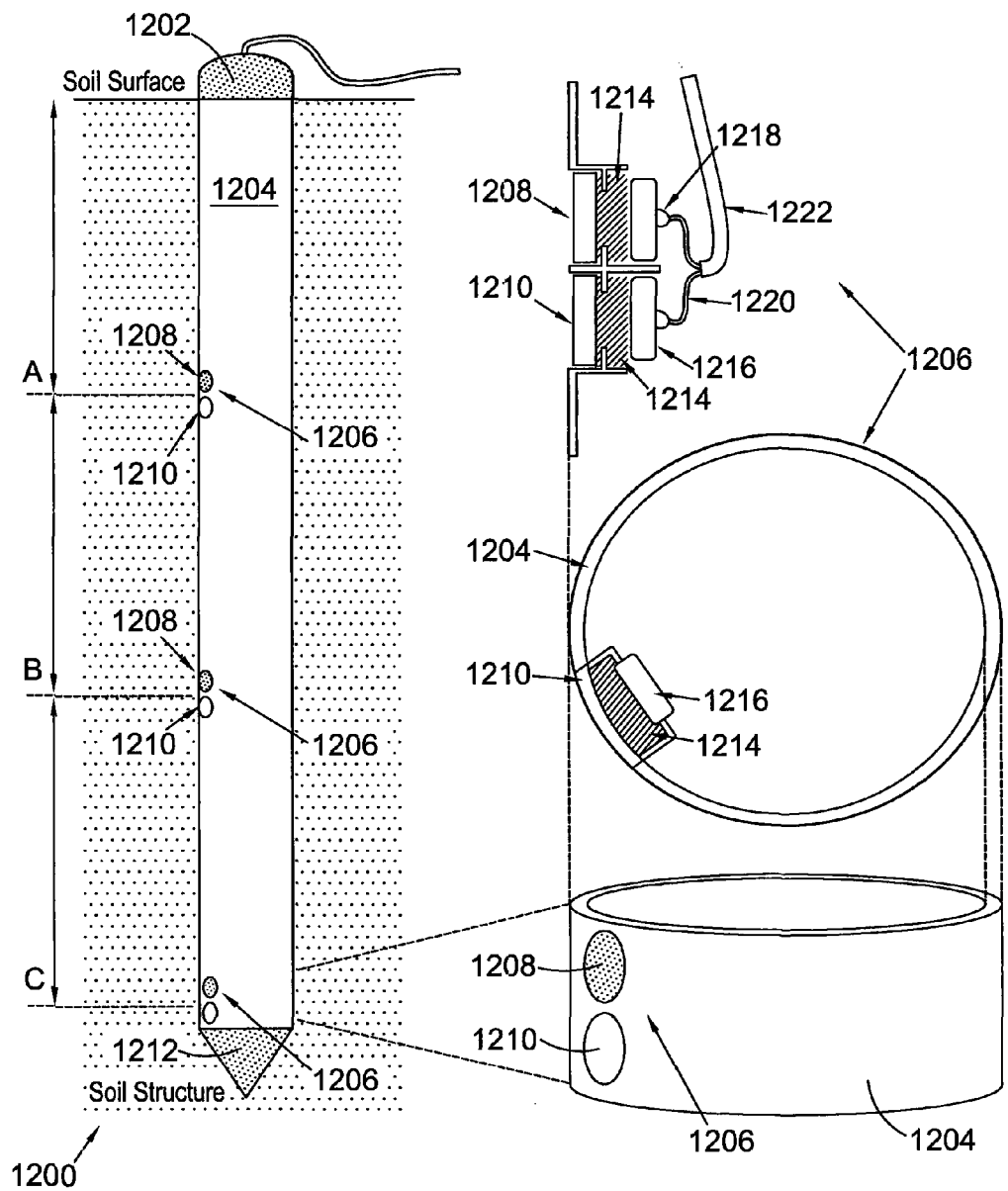
FIG. 12a illustrates a probe comprising multiple 'button-style' soil chemistry sensors for measuring soil chemistry at multiple depths within a soil structure, according to an embodiment of the invention.

Measuring Soil Chemistry In Situ at Different Depths with 'Button-Style' Sensors The above-described probes use soil chemistry sensors in either a vertical or lateral arrangement within the probe. In a further alternative embodiment of the probe, the soil sensors resemble a button along a length of the probe. FIG. 12*a* illustrates a probe 1200 comprising multiple 'button-style' soil chemistry sensors for measuring soil chemistry at multiple depths within a soil structure.

The probe 1200 comprises a tube part 1204 and multiple 'button-style' sensors 1206 disposed along the length of the probe. Membranes of each sensor 1206 are flush or substantially flush with the external surface of probe 1200. The sensors 1206 are positioned at fixed points along the probe, such that the first sensor measures soil chemistry at a depth A below the soil surface, the second sensor measures soil chemistry at a depth B and so on. Thus, the probe is configured to measure the soil chemistry at these fixed depths below the soil surface. Probes of different lengths and/or different sensor positions may be fabricated to take measurements at alternative depths. At the bottom end of probe 1200 is a pointed tip part 1212. The pointed tip 1212 is preferably a sharp metal tip which helps insertion of the probe 1200 into a soil structure, and minimises damage to the end of probe 1200 and the sensors inside. The top end of probe 1200 is sealed by a plastic cap 1202 to prevent water/soil water from entering probe 1200 from the top.

Figure 12B:
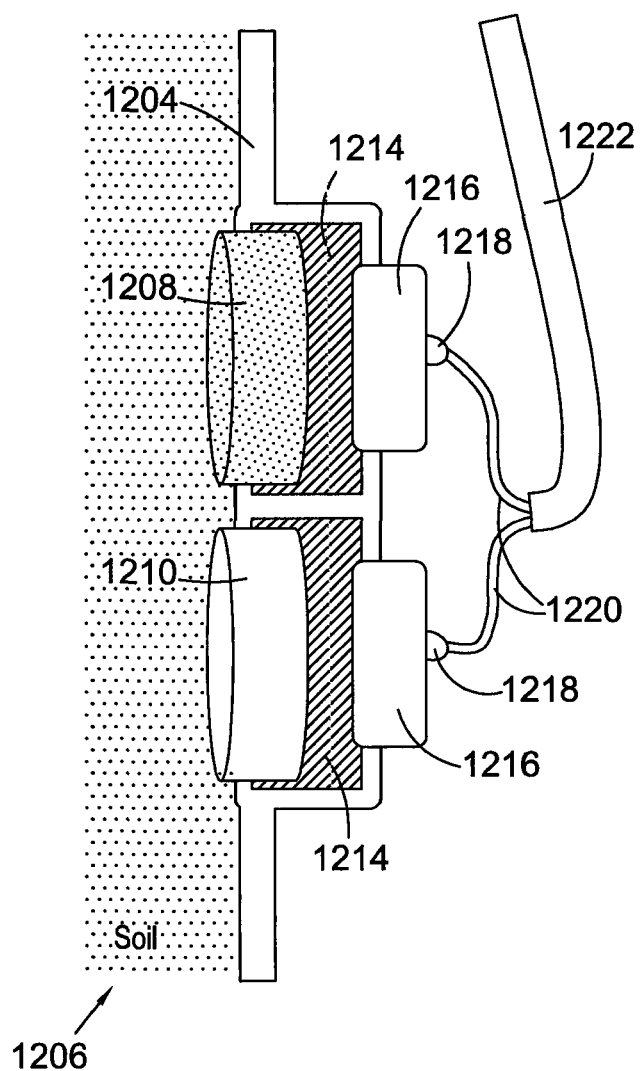

As shown in FIG. 12*a* and in the zoomed-in view of FIG. 12*b*, the sensor 1206 is a double button style sensor, as each membrane is provided by a separate button-shaped sensor. Reference membrane 1208 and ion-selective membrane 1210 both have a button shape. The membranes 1208 and 1210 are positioned side-by-side so that they are as close as possible and are measuring the soil chemistry at substantially the same position in the soil structure. While in FIG. 12*a* the membranes 1208 and 1210 are positioned one above the other, they may in embodiments be positioned side-by-side. Each membrane 1208, 1210 is coupled to a conductive (e.g. silver) contact element 1216 via a conductive gel 1214. Each contact 1216 is coupled to wires 1220 via a soldering point 1218. Wires 1220 may be wrapped in an insulating material 1222 for connection to a data logger (not shown).

Figure 12C:
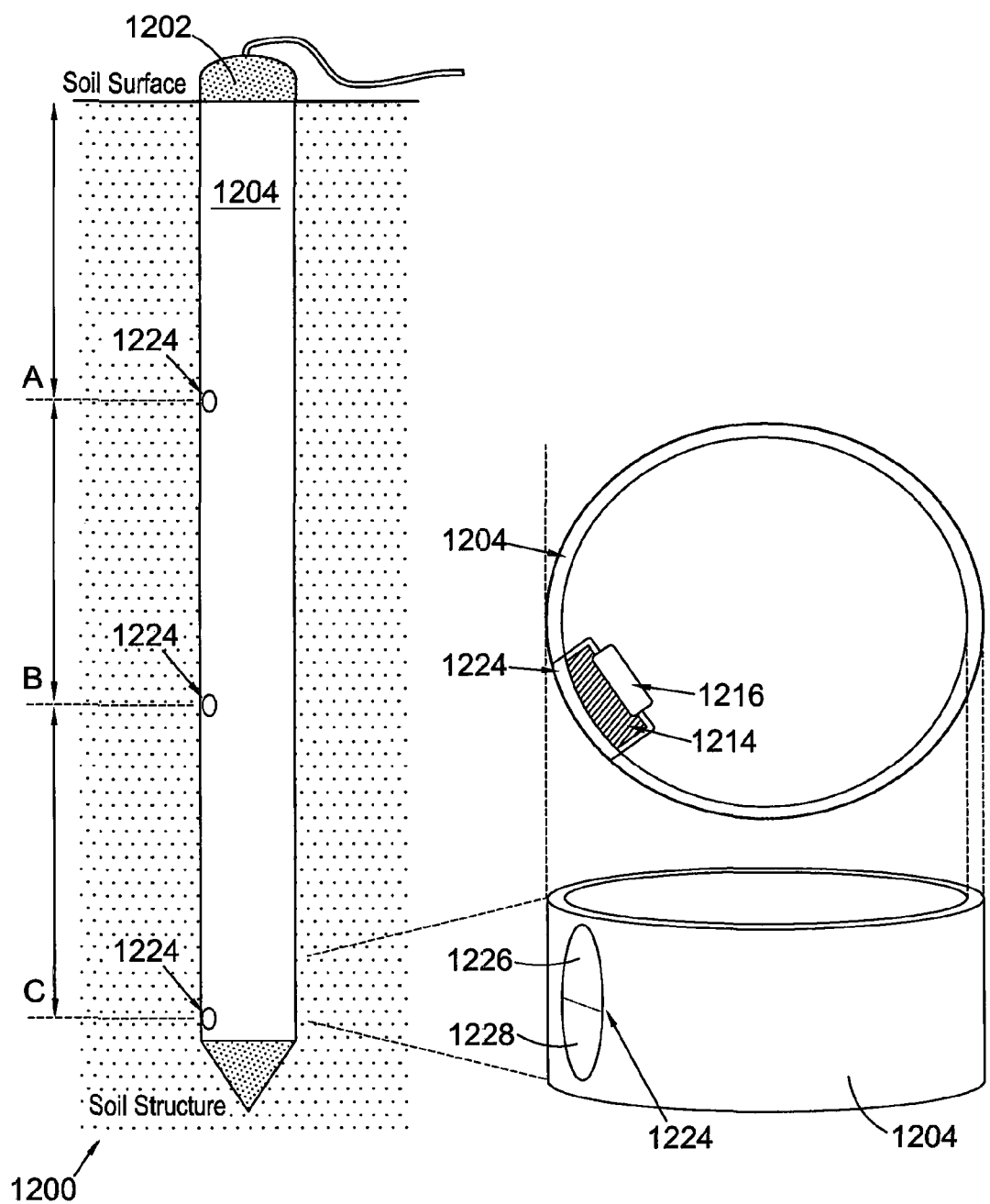
FIG. 12c illustrates a probe comprising multiple 'button-style' soil chemistry sensors for measuring soil chemistry at multiple depths within a soil structure, according to an alternative embodiment of the invention.
Figure 12D:
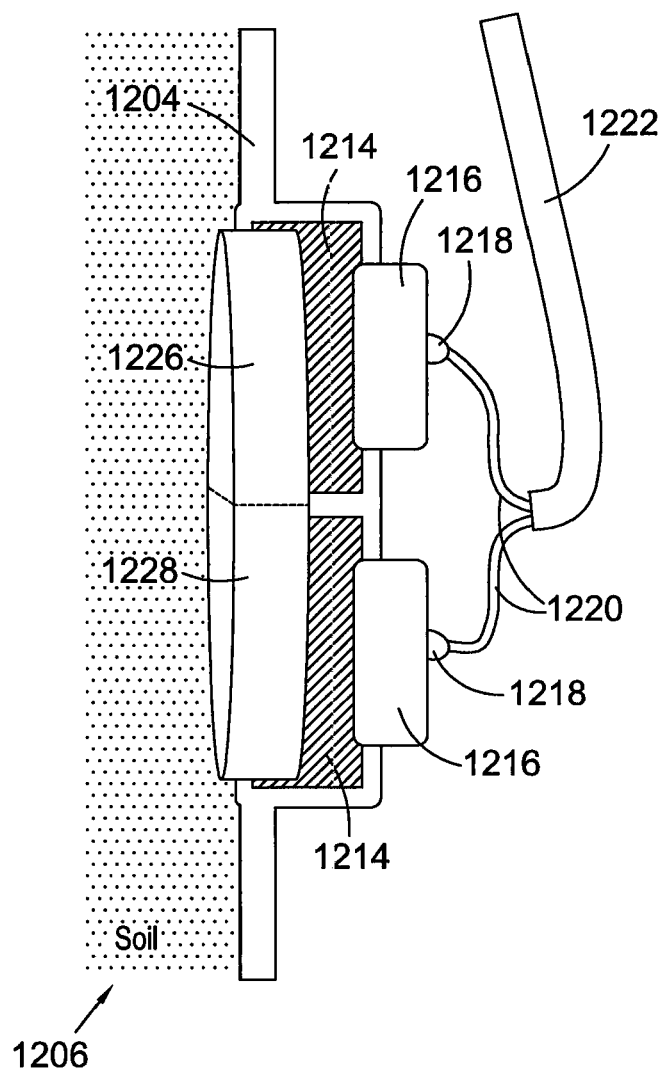
FIG. 12d shows a zoomed-in view of the 'button-style' soil chemistry sensor of FIG. 12c.

Turning now to FIGS. 12*c* and 12*d*, these illustrate an alternative arrangement of probe 1200, also comprising multiple 'button-style' soil chemistry sensors for measuring soil chemistry at multiple depths within a soil structure. Here, probe 1200 comprises a tube part 1204 and multiple single button style sensors 1224. A single button shaped sensor 1224 provides both the reference and ion-selective membranes. Both membranes are cast on a single button shaped sensor. As shown in more detail in FIG. 12*d*, the sensor 1224 comprises two portions, where one portion provides a reference membrane 1226 and the second portion provides an ion-selective membrane 1228. While the two portions are shown one above the other, they may in embodiments be positioned side-by-side (i.e. the button sensor 1224 may be rotated by 90°). Each membrane 1226, 1228 is coupled to a conductive (e.g. silver) contact element 1216 via a conductive gel 1214. Each contact 1216 is coupled to wires 1220 via a soldering point 1218. Wires 1220 may be wrapped in an insulating material 1222 for connection to a data logger (not shown).

A single or double button-shaped sensor is detachably 'plugged' into an aperture provided along the length of the tube part 1204. Advantageously, this enables the sensors to be detached and replaced if faulty or if a different ion is to be measured. Furthermore, each membrane of the double button-shaped sensor can be removed separately.

No doubt many other effective alternatives will occur to the skilled person. For example an embodiment of the sensor can be used not in situ in the soil but to measure nitrate levels in soil on-site. In this case a core sample may be dug up and shaken up with water to obtain a measurement on the spot. Similarly an embodiment of the sensor can be used may be employed to measure nitrate levels in leaves (again shaken up with water), which has value in research and breeding as well as in farm crop testing.

It will be understood that the invention is not limited to the described embodiments and encompasses modifications apparent to those skilled in the art and lying within the spirit and scope of the claims appended hereto.

The invention claimed is:

1. A soil chemistry sensor for in-situ soil chemistry sensing, the sensor comprising a probe incorporating a first, ion-selective electrode and a second, reference electrode, wherein said ion-selective electrode comprises a first-electrode housing defining a first lumen having an ion-selective plug towards a distal end, said first-electrode including a first conductor in a first electrolyte, wherein said reference electrode comprises a second electrode housing defining a second lumen having a porous reference electrode plug towards a distal end, said second electrode including a second conductor in a second electrolyte, wherein said ion-selective plug and said porous reference electrode plug are within 10 mm of one another, and wherein said porous reference electrode plug and said ion-selective plug each comprise a polymer.

2. The soil chemistry sensor as claimed in claim 1 wherein said porous reference electrode plug and said ion-selective plug each comprise the same said polymer.

3. The soil chemistry sensor as claimed in claim 1 wherein said polymer is a solvent-cast polymer.

4. The soil chemistry sensor as claimed in claim 1 wherein said polymer is PVC.

5. The soil chemistry sensor as claimed in claim 1 wherein said polymer of said porous reference electrode plug includes one or more additives to lower an electrical resistance of said porous reference electrode plug.

6. The soil chemistry sensor as claimed in claim 1 wherein said first and second electrodes are sealed within a waterproof enclosure.

7. The soil chemistry sensor as claimed in claim 6 wherein said waterproof enclosure comprises cold-shrink tubing.

8. The soil chemistry sensor as claimed in claim 1 wherein said second, reference electrode comprises a double junction electrode including a second electrode chamber connecting with said second lumen via a second porous plug, said inner second electrode chamber containing said second conductor in said second electrolyte.

9. The soil chemistry sensor as claimed in claim 8 wherein said second porous plug comprises said polymer.

10. The soil chemistry sensor as claimed in claim 1 wherein said first-electrode housing and said second-electrode housing each comprise plastic.

11. The soil chemistry sensor as claimed in claim 1 wherein said ion-selective plug is a nitrate-selective plug.

12. The soil chemistry sensor as claimed in claim 1 further comprising fastening means around said distal ends of said first and second electrodes to inhibit said distal ends from moving apart.

13. The soil chemistry sensor as claimed in claim 12 wherein said ion-selective plug and said porous reference electrode plug are within 5 mm of one another.

14. The soil chemistry sensor as claimed in claim 1 further comprising said moisture sensing means.

15. The soil chemistry sensor as claimed in claim 1 further comprising a voltage sensor coupled to said first and second conductors, and a wireless network transmitter coupled to said voltage sensor to enable wireless collection of soil chemistry data from said soil chemistry sensor.

16. The plurality of soil chemistry sensors each as claimed in claim 1, coupled to one or more voltage sensors, wherein said one or more voltage sensors are coupled to one or both of i) a shared data logger, and ii) a shared wireless network transmitter to enable wireless collection of soil chemistry data from said soil chemistry sensors.

17. A method of collecting soil chemistry data from soil, the method comprising inserting the soil chemistry sensor of claim 1 into the soil to be measured.

18. The method as claimed in claim 17 further comprising measuring one or both of a mixture content of said soil and an ionic strength of water in said soil, using said soil chemistry sensor, and compensating a signal from said soil chemistry sensor responsive to a result of said measuring.

19. The method as claimed in claim 17 comprising providing a plurality of said soil chemistry sensors at different depths within said soil.

20. The method of collecting soil chemistry data as claimed in claim 17 further comprising determining when to apply fertilizer to a plant, wherein said determining comprises:

sensing a level of nutrient at a plurality of different depths in the vicinity of said plant, using the sensor/probe, wherein said depths identify a nutrient depletion zone, said nutrient depletion zone comprising a region, defined by depth, where uptake of said nutrient by said plant is relatively greater;

determining a ratio of sensed nutrient levels between at least two of said different depths to determine an uptake of said nutrient by said plant from a relative depletion of said nutrient at one of said depths with respect to another; and determining when to apply said fertilizer based on said determined ratio.

* * * * *